United States Patent
Larsen et al.

(10) Patent No.: US 8,297,959 B2
(45) Date of Patent: Oct. 30, 2012

(54) SYSTEMS FOR PRODUCING MULTILAYERED PARTICLES, FIBERS AND SPRAYS AND METHODS FOR ADMINISTERING THE SAME

(75) Inventors: Gustavo Larsen, Denton, NE (US); Ruben Spretz, Lincoln, NE (US); Raffet Velarde-Ortiz, Lincoln, NE (US); David Vu, Lincoln, NE (US); Luis Nunez, Chicago, IL (US)

(73) Assignee: Terapia Celular, LN, Inc., Denton, NE (US)

( * ) Notice: Subject to any disclaimer, the term of this patent is extended or adjusted under 35 U.S.C. 154(b) by 0 days.

(21) Appl. No.: 11/743,560

(22) Filed: May 2, 2007

(65) Prior Publication Data
US 2007/0296099 A1 Dec. 27, 2007

Related U.S. Application Data

(60) Provisional application No. 60/746,311, filed on May 3, 2006, provisional application No. 60/886,255, filed on Jan. 23, 2007.

(51) Int. Cl.
*B29B 9/10* (2006.01)
*A61J 3/07* (2006.01)

(52) U.S. Cl. ............. 425/5; 425/3; 425/6; 425/7; 425/8; 264/4; 264/4.1; 264/5; 264/13

(58) Field of Classification Search .................. 425/3, 5, 425/6, 7, 8, 10; 264/4.3, 4.32, 4.33, 4.1, 264/4.4, 4.6, 4.7, 5, 13
See application file for complete search history.

(56) References Cited

U.S. PATENT DOCUMENTS

| 2,275,154 | A | * | 3/1942 | Merrill et al. .................. 264/4 |
| 2,387,747 | A | | 10/1945 | Cowley |
| 2,766,478 | A | * | 10/1956 | Raley, Jr. et al. .............. 264/4 |
| 2,911,672 | A | * | 11/1959 | Van Erven Dorens et al. ... 264/4 |
| 3,160,686 | A | * | 12/1964 | Doyle et al. .................. 264/4 |
| 3,310,612 | A | * | 3/1967 | Somerville, Jr. .............. 264/4 |
| 3,710,933 | A | * | 1/1973 | Fulwyler et al. ............. 209/3.1 |
| 3,975,194 | A | * | 8/1976 | Farnand et al. ............... 419/5 |
| 4,119,739 | A | * | 10/1978 | Barwick et al. .............. 426/573 |
| 4,162,282 | A | * | 7/1979 | Fulwyler et al. .............. 264/9 |
| 4,201,691 | A | * | 5/1980 | Asher et al. .................. 516/10 |

(Continued)

FOREIGN PATENT DOCUMENTS
WO WO 2004/103510 A2 * 12/2004
(Continued)

OTHER PUBLICATIONS

International Search Report and Written Opinion, dated Jan. 24, 2008.

*Primary Examiner* — Joseph Del Sole
*Assistant Examiner* — Seyed Masoud Malekzadeh
(74) *Attorney, Agent, or Firm* — Howard & Howard Attorneys PLLC

(57) ABSTRACT

Capsules and particles with at least one encapsulated and/or entrapped agent, such as therapeutic agent, imaging agents, and other constituents may be produced by electrohydrodynamic processes. More particularly, the agent encapsulated in a vehicle, capsule, particle, vector, or carrier may maximize treatment and/or imaging of malignant cancers while minimizing the adverse effects of treatment and/or imaging.

18 Claims, 19 Drawing Sheets

U.S. PATENT DOCUMENTS

| | | | | |
|---|---|---|---|---|
| 4,251,195 A | * | 2/1981 | Suzuki et al. | 425/6 |
| 4,290,993 A | | 9/1981 | Maringer | |
| 4,303,736 A | * | 12/1981 | Torobin | 428/403 |
| 4,315,720 A | | 2/1982 | Ueda et al. | |
| 4,323,523 A | | 4/1982 | Ueda et al. | |
| 4,374,074 A | | 2/1983 | Ueda et al. | |
| 4,415,512 A | * | 11/1983 | Torobin | 264/9 |
| 4,419,383 A | | 12/1983 | Lee | |
| 4,426,525 A | | 1/1984 | Hozumi et al. | |
| 4,613,076 A | | 9/1986 | Dietz et al. | |
| 4,689,075 A | * | 8/1987 | Uda et al. | 75/346 |
| 4,762,975 A | * | 8/1988 | Mahoney et al. | 219/69.1 |
| 4,902,450 A | * | 2/1990 | Morrison | 264/4 |
| 4,981,625 A | * | 1/1991 | Rhim et al. | 264/13 |
| 5,081,048 A | | 1/1992 | Okahata et al. | |
| 5,121,692 A | * | 6/1992 | DiCarlo | 102/439 |
| 5,122,670 A | * | 6/1992 | Mylchreest et al. | 250/423 R |
| 5,126,381 A | * | 6/1992 | Liscomb | 522/3 |
| 5,143,662 A | | 9/1992 | Chesterfield et al. | |
| 5,209,978 A | * | 5/1993 | Kosaka et al. | 428/402.2 |
| 5,411,480 A | * | 5/1995 | Kriesel | 604/133 |
| 5,558,837 A | * | 9/1996 | Tsukishima | 422/527 |
| 5,595,758 A | | 1/1997 | Adusumilli et al. | |
| 5,648,099 A | * | 7/1997 | Batich et al. | 424/497 |
| 5,776,940 A | * | 7/1998 | Daluge et al. | 514/263.34 |
| 5,783,214 A | | 7/1998 | Royer | |
| 5,976,428 A | * | 11/1999 | Richley | 264/10 |
| 6,033,888 A | * | 3/2000 | Batich et al. | 435/178 |
| 6,103,271 A | * | 8/2000 | Morrison et al. | 424/490 |
| 6,110,538 A | * | 8/2000 | Sheridon | 427/457 |
| 6,143,211 A | * | 11/2000 | Mathiowitz et al. | 264/4 |
| 6,234,402 B1 | * | 5/2001 | Ganan-Calvo | 239/8 |
| 6,242,230 B1 | * | 6/2001 | Batich et al. | 435/178 |
| 6,248,378 B1 | * | 6/2001 | Ganan-Calvo | 426/89 |
| 6,298,272 B1 | * | 10/2001 | Peterfeso et al. | 607/120 |
| 6,361,298 B1 | * | 3/2002 | Kiefer et al. | 425/5 |
| 6,377,387 B1 | * | 4/2002 | Duthaler et al. | 359/296 |
| 6,422,687 B1 | * | 7/2002 | Jacobson | 347/55 |
| 6,696,090 B1 | * | 2/2004 | Nilsson et al. | 424/489 |
| 6,832,733 B2 | * | 12/2004 | Engel | 239/145 |
| 6,989,169 B2 | * | 1/2006 | Ripoll et al. | 426/235 |
| 7,029,880 B2 | | 4/2006 | Weigel et al. | |
| 7,214,255 B2 | * | 5/2007 | Brewster et al. | 75/351 |
| 7,258,428 B2 | * | 8/2007 | Reddy et al. | 347/68 |
| 7,279,322 B2 | * | 10/2007 | Pui et al. | 435/285.2 |
| 7,294,309 B1 | * | 11/2007 | Goldberg et al. | 422/100 |
| 7,498,063 B2 | * | 3/2009 | Pui et al. | 427/479 |
| 7,588,703 B2 | * | 9/2009 | Morrison | 264/4.1 |
| 2004/0069632 A1 | * | 4/2004 | Ripoll et al. | 204/450 |
| 2004/0131673 A1 | | 7/2004 | Coffee et al. | |
| 2004/0155612 A1 | * | 8/2004 | Krichtafovitch | 315/500 |
| 2004/0161498 A1 | * | 8/2004 | Ripoll et al. | 426/89 |
| 2005/0151490 A1 | * | 7/2005 | Krichtafovitch | 315/506 |
| 2006/0075676 A1 | * | 4/2006 | Turner | 43/17.6 |
| 2006/0093678 A1 | * | 5/2006 | Chickering et al. | 424/489 |

FOREIGN PATENT DOCUMENTS

| | | |
|---|---|---|
| WO | WO 2004103510 A2 * | 12/2004 |
| WO | WO 2007/110783 | 10/2007 |

* cited by examiner

Panel I          Panel II

SYSTEMS FOR PRODUCING MULTILAYERED PARTICLES, FIBERS AND SPRAYS AND METHODS FOR ADMINISTERING THE SAME

CROSS-REFERENCE TO RELATED APPLICATIONS

This application claims priority to and the benefit of U.S. Provisional Application Ser. No. 60/746,311, filed May 3, 2006, and U.S. Provisional Application Ser. No. 60/886,225, filed Jan. 23, 2007, the disclosures of which are expressly incorporated herein by reference in their entirety.

BACKGROUND

1. Field of the Invention

The invention relates to systems and methods for producing capsules and particles with at least one encapsulated and/or entrapped agent, such as therapeutic agent, imaging agents, and other constituents. More particularly, the agent encapsulated in a vehicle, capsule, particle, vector, or carrier may maximize treatment and/or imaging of malignancy while minimizing the adverse effects of treatment and/or imaging.

2. Related Art

Cancer is a class of diseases or disorders characterized by uncontrolled division of cells and the ability of these to spread, either by direct growth into adjacent tissue through invasion, or by implantation into distant sites by metastasis. Cancer may affect people at all ages, but risk tends to increase with age. It is one of the principal causes of death in developed countries.

For example, according to the National Cancer Institute, breast cancer affected between 12 and 13 per every 10,000 women in 2003. Although imaging and early diagnostic tools have been improving over the past two decades, current breast cancer early detection is far from infallible, especially when using mammograms in younger women. While magnetic resonance imaging (MRI and ultrasound) and laser-based imaging techniques have been used or evaluated, the issue for best-possible contrast between healthy and cancerous tissue for any imagining technique is a longstanding one.

A current challenge facing scientists is determining how to design a therapeutic or an imaging agent and its vehicle, vector or carrier in order to maximize treatment and imaging of malignant cancers in patients while minimizing the adverse effects of treatment. Moreover, the selective delivery of therapeutic agents to a desired part of the body is also a nontrivial issue. Current treatments may lead to insufficient tumor distribution or therapeutic agents and often cause adverse effects on patients. Systemic injections of therapeutic agents carry consequences associated with their nonspecific dispersion in the body and have a limited therapeutic agent distribution throughout the targeted malignancy. One approach to overcome these short comings is to design an effective therapeutic or imaging agent delivery vehicle by making vesicles or capsules containing the desired therapeutic agent.

Formation of vesicles or capsules that are small enough to be delivered into the human body by means of inhalation, injection or permeation through the skin has received significant attention. The outer skin or shell of the vesicles may be chemically functionalized with receptors and other species to selectively target certain organs. There are several methodologies available, such as electrospray and two-capillary jet systems to fabricate small vesicles.

Emulsion-polymerization technologies, such as DC coaxial electrospray, AC coaxial electrospray, and electrohydrodynamics (EHD) are well known methods that may produce micron-sized capsules. In general, a solution containing the target compound or compounds to be encapsulated, also called "encapsulates," is emulsified into another fluid to solution having at least one substance capable of forming a shell or envelope around the encapsulate dispersed droplets. Although emulsion-polymerization methods are relatively scalable, there are several limitations associated with the methods, such as the inability to encapsulate the targets in a quantitative manner, and the high-shear production of emulsions may compromise the integrity of mechanically delicate encapsulates, such as biological constituents such as proteins, genetic material, and other molecules of biological origin.

Coaxial electrospray based on application of DC electrical potentials between a coaxial capillary fixture delivering the encapsulate-containing core liquid and a shell-forming liquid precursor, and a collector surface or counter-electrode, has the ability to produce vesicles in the micrometer and sub-micrometer range. Although DC coaxial electrospray may be relatively gentle to biological encapsulates, its major limitation is that it lacks simplicity in equipment, design, scalability, and thus cost effectiveness.

As an alternative to DC based electrospray, AC electrospray may be employed. For example, AC electrospray may be used to produce encapsulates entrapped within a bioabsorbable biopolymeric matrix, such as polylactic acid. AC electrospray yields essentially an electrically neutral electrospray. While there are advantages associated with charge neutrality, such as decreased ability of the particles or electrospray droplets to absorb indiscriminately over non-targeted surfaces, and avoidance of a potential charge buildup problem. One disadvantage of AC electrospray is that it produces undesirably large particles having sizes well above one micron. For many medical applications, such as penetration of the blood brain barrier, AC electrospray derived particles are unacceptably large.

In addition to electrospray methodologies, coaxial liquid jet system combined with sol-gel chemistry, such as EHD, may be employed to fabricate vesicles or capsules. Use of coaxial, two-capillary coaxial arrangements to simultaneously deliver two fluids in the presence of electric field gradients are well known in the art.

Briefly, in this method, the chemistry and physical properties of the two fluids and the values of variables such as electric field strength and flow rates of the two fluids may determine the structure of matter collected onto a collector electrode, which may be located at a distance from the exit region of the two-capillary coaxial arrangement. At the exit region, the compound two-fluid structure may form an electrified meniscus that may adopt various shapes, such as a Taylor cone.

FIG. 1, which illustrates a fluid flow generated by a two-coaxial capillary system of the prior art, depicts a two-fluid stream 100 in the presence of electric field gradients, where the internal fluid 104 is enveloped by the external fluid 106. The quasi-conical Taylor cone structure 108 issues an electrified compound two-fluid jet from its apex 110. here, the electrified liquid jet experiences thinning due to same-charge repulsion effects. Moreover, the thinning of the jet may be a function of the physical properties of the two liquids such as, dielectric constants, viscosities, conductivities and surface tensions. Although differentiated two-fluid structures may occur when fluid 104 and fluid 106 do not mix, they may also occur when fluid 104 and fluid 106 are miscible or partially miscible, because both fluids flow under the so-called laminar flow regime.

Laminar flows may be non-turbulent, which may minimize mixing between flowing fluid layers. Thus, since the two fluids may not mix to the point of forming a single fluid phase, the thinning electrified two-fluid jet may enter into a chaotic path resembling whipping phenomena. At a point along its path toward a collection zone or collector body 112, the compound two-fluid jet may experience an electrical charge oscillatory phenomenon known as Rayleigh instability. This may cause the compound two-fluid jet to no longer experience progressive thinning, but an oscillatory thinning and thickening regime which may eventually lead to jet breakup into a droplet-in-droplet regime, or compound electrospray regime.

The chemical and physical properties of the two fluids may be controlled to produce a variety of structures collected at the collection zone or collector electrode 112. For example, if fluid 106 yields a solid structure through solvent evaporation and precipitation of a solid phase, fluid 104 may be encapsulated into structures such as hollw fibers, hollow beaded fibers or capsules, for example. Alternatively, the chemical and physical properties of the two liquids may be adjusted to cause no solidification of fluid 104 and fluid 106, solidification of one of the two fluids, or solidification of both fluids, during the time of travel of the compound charged structures from the two-fluid electrified meniscus to the collection zone 112.

Referring to FIG. 1, regions 3, 4, and 5 are shown. If certain physiochemical phenomena lead to solidification of fluid 106 in region 3, tubular structures encapsulating fluid 104 inside a solid shell formed from fluid 106 may be obtained. If, however, solidification phenomena in fluid 106 occur in region 4, hollow beaded fibers with encapsulated fluid 104 may be obtained. Alternatively, if solidification phenomena in fluid 106 occur in region 5, capsules with encapsulated fluid 104 may be obtained. Wetted fibers, wetted beaded fibers or wetted particles may result in regions 3, 4, and 5, respectively, in cases where fluid 104 solidifies but fluid 106 does not. Core-shell solid structures may result when both fluids solidify prior to reaching the collection zone.

Although coaxial two-capillary systems may be employed to produce the core-shell structures, described above, there are several disadvantages associated with the conventional systems. In particular, when a direct, parallel scale-up of the process to increase process throughput is attempted a microfabrication problem occurs. For instance, a typical range of internal diameters for the inner and outer capillaries are about 0.1 to about 0.3 mm and about 0.3 to about 1.0 mm, respectively, In order to build an instrument consisting of many such coaxial, two-capillary fixtures for scaled up production of a desired core-shell structure, it is necessary to produce each individual fixture with inner and outer capillaries aligned as close to coaxial as possible, and also with high reproducibility in their diameters. With modern micro-fabrication techniques such challenge may be met, however, these techniques are very complex and not cost effective.

In particular, a conventional way to manage fluid flow through many orifices, capillaries, conduits or two-capillary coaxial fixtures is by using one means for forcing flow through all same fluid orifices, capillaries, conduits or two-capillary coaxial fixtures, not by controlling the fluid flow rate through each individual fluid flow path. This is the reason why, for example, fabricating a parallel scaled up production of a desired core-shell structure is difficult and expensive. If there is variability in diameter from inner or outer capillary of one two-capillary coaxial fixture to another in excess of about 2% or 3%, it is not possible to produce a desired core-shell structure without the occurrence of undesirable structures. With such prior art two-capillary fixture, small differences in the overall pressure drop profiles of the inner and outer capillaries also causes undesirable effects.

SUMMARY OF THE INVENTION

The invention satisfies the above needs by providing systems and methods for fabricating capsules with entrapped or encapsulated therapeutic agents and/or imaging agents. More particularly, the systems and methods of the invention permits a wider range of capsule size, keeps chemical interactions leading to degradation of therapeutic agents and/or imaging agents to sufficiently low and acceptable levels, involves less manufacturing steps, and is more cost effective than conventional methods.

According to one aspect of the invention, an electrohydrodynamic system ofr producing a capsule having at least one encapsulated agent is provided. The system may include a hollow tube having an interior configured to receive a core fluid, a fluid source surrounding said hollow tube, a core fluid supply tube arranged to supply the core fluid to said interior of said hollow tube, a shell fluid supply tube arranged to supply the shell fluid to said shell fluid source, and an electric potential source to subject the core fluid and the shell fluid to an electric potential to cause the fluids to form a jet including an at least two-fluid electrically charged fluid. The system may include a core fluid reservoir. The system may also include a shell fluid reservoir. The encapsulated agent may be at least one of a therapeutic agent and an imaging agent.

In a particular aspect, the system may also include a collector electrode positioned above the fluid bath. Additionally, they system may include an extractor body positioned between the fluid bath and the collector electrode.

In a more particular aspect, the fluid source may be a fluid bath. The fluid source may also be a porous material. The porous material may be a sponge. Moreover, the fluid source may be a plurality of tubes.

According to one aspect of the invention, a system for producing a capsule having at least one encapsulated agent is provided. The system may include plurality of hollow tubes, an encasement surrounding said plurality of hollow tubes, a core fluid supply tube arranged to supply the core fluid to the interior of said plurality of hollow tubes, a shell fluid supply tube arranged to supply the shell fluid, and an electric potential source to subject the core fluid and the shell fluid to an electric potential to cause the fluids to form a jet having an at least two-fluid electrically charged fluid. The system may also include a collector electrode. Moreover, the system may also include an extractor body.

In a further aspect, the system of the invention may include a core fluid reservoir. Moreover, the system may also include a shell fluid reservoir.

In a specific aspect, the plurality of hollow tubes may be circumferentially arranged in said encasement. The plurality of hollow tubes may also be linearly arranged linearly arranged in said encasement comprising at least two plates. The encasement may be configured to receive and delivery the shell fluid. The shell supply tube may be configured and arranged to supply the shell fluid to a space between to said plurality of hollow tubes.

In a particular aspect, the system of the invention may be configured to perform upward flow electrohydrodynamics. Alternatively, the system of the invention may be configured to perform downward flow electrohydrodynamics.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification; illustrate embodiments of the invention and together with the detailed description serve to explain the principles of the invention. No attempt is made to show structural details of the invention in more detail than may be necessary for a fundamental understanding of the invention and various ways in which it may be practiced.

FIG. 6B is a cross-section of FIG. 6A.

DETAILED DESCRIPTION OF THE INVENTION

Figure 1:
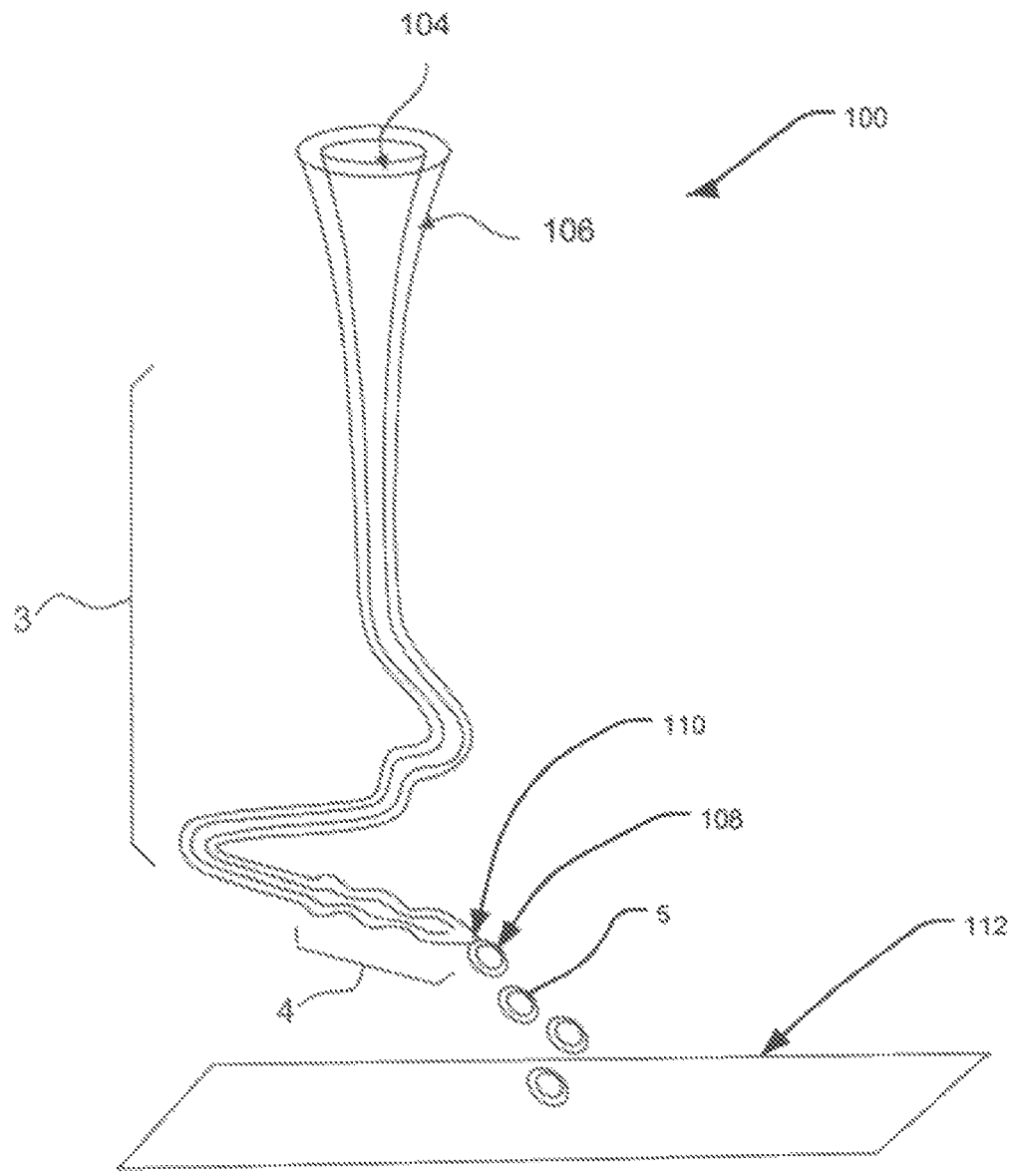
FIG. 1 is a schematic showing a two-fluid electrified jet, which is a stream of fluids that may include at least two distinct fluid layers, according to principles of the invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a, " "an," and "the" include the plural reference unless the context clearly dictates otherwise. this, for example, a reference to "a capsule" is a reference to one or more capsules and equivalents thereof known to those skilled in the art.

Unless defined otherwise, all technical and scientific terms used herein have the same meaning as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, temperature, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically. particular methods, devices, and materials are described, although any methods and materials similar or equivalent to those described herein can be used in the practice or testing of the invention. All references referred to herein are incorporated by reference herein in the entirety.

Definitions

BSA is bovine serum albumin
CED is convection enhanced delivery
CFM is confocal fluorescence microscopy EHD is electrohydrodynamics
PBS is phosphate-buffer saline
PEG is Poly(ethylene glycol)
PLA is poly(lactic acid)
PLC is polycaprolactone
PLGA is poly(lactic-co-glycolic acid)

The terms "active agent," "drug," "therapeutic agent," and "pharmacologically active agent" are used interchangeable herein to refer to a chemical material or compound which, when administered to an organism (human or animal) induces a desired pharmacologic effect. Included are derivatives and analogs of those compounds or classes of compounds specifically mentioned that also induce the desired pharmacologic effect. In particular, the therapeutic agent may encompass a single biological or abiological chemical compound, or to a combination of biological and abiological compounds that may be required to cause a desirable therapeutic effect.

By "pharmaceutically acceptable carrier" is meant a material or materials that are suitable for drug administration and not biologically or otherwise undesirable, i.e., that may be administered to an individual along with an active agent without causing any undesirable biological effects or interacting in a deleterious manner with any of the other components of the pharmaceutical formulation in which it is contained.

Similarly, a "pharmacologically acceptable" salt, ester or other derivative of an active agent as provided herein is a salt, ester or other derivative that is not biologically or otherwise undesirable.

By the terms "effective amount" or "therapeutically effective amount" of an agent as provided herein are meant a nontoxic but sufficient amount of the agent to provide the desired therapeutic effect. The exact amount required will vary from subject to subject, depending on the age, weight, and general condition of the subject, the severity of the condition being treated, the judgment of the clinician, and the like. thus, it is not possible to specify an exact "effective amount." However, an appropriate "effective" amount in any individual case may be determined by one of ordinary skill in the art using only routine experimentation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, the present method of "treating" individuals with cancer, as the term "treating" is used herein, encompasses treatment of cancer in a clinically symptomatic individual.

The terms "condition," "disease" and "disorder" are used interchangeably herein as referring to a physiological state that can be detected, prevented or treated by administration of a therapeutic agent as described herein. Exemplary diseases and conditions may include, but not limited to, cancer such as breast cancer, glioma, pancreatic cancer, leukemia, and lymphoma.

The term "patient" as in treatment of "a patient" refers to a mammalian individual afflicted with or prone to a condition, disease or disorder as specified herein, and includes both humans and animals.

The term "nucleic acid," as used herein may include an oligonucleotide, nucleotide, or polynucleotide, and fragments thereof, and to DNA or RNA of genomic or synthetic origin which may be single- or double-stranded, and represent the sense or antisense strand, to peptide nucleic acid (PNA), to small interfering RNA (siRNA) molecules, or to any DNA-like or RNA-like material, natural or synthetic in origin.

The term "transfection," as used herein includes the process of introducing a DNA expression vector into a cell. Various methods of transfection are possible including microinjection or lipofection.

The term "transformation," as used herein generally refers to a process by which exogenous DNA enters and changes a recipient cell. It may occur under natural or artificial conditions using various methods known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, and lipofection.

Antisense gene: an antisense gene is constructed by reversing the orientation of the gene with respect to its promoter so that the antisense strand is transcribed.

Antisense RNA: an RNA molecule complementary to a particular RNA transcript that can hybridize to the transcript and block its function.

The term "functional equivalent," as used herein generally refers to a protein or nucleic acid molecule that possesses functional or structural characteristics that is substantially similar to a heterologous protein, polypeptide, enzyme, or nucleic acid. A functional equivalent of a protein may contain modifications depending on the necessity of such modifications for the performance of a specific function. The term "functional equivalent" is intended to include to "fragments," "mutants," "hybrids," "variants," "analogs," or "chemical derivatives" of a molecule.

"Compound electrified fluid jet" as used herein generally refers to a stream of fluid composed of at least two distinct fluid layers. For example, when two fluids are used to form a compound electrified jet by EHD, the outer fluid is the fluid precursor the shell of the capsule made by the compound electrified fluid jet EHD method and the inner fluid is the precursor for the core of the capsule.

According to the invention, an agent is "encapsulated" when the capsule has at least one core region and at least one particle shell region in a layered architecture. The capsule may further contain at least one agent, such as a therapeutic agent or an imaging agent.

According to the invention, an agent is "entrapped" when the agent is dispersed within a biocompatible matrix composed of one or more biocompatible polymers, for example, and distinct onion-like layers are not apparent.

The term "carcinoma" as used herein generally refers to malignant tumors derived from epithelial cells. This group may represent the most common cancers, including the common forms of breast, prostate, lung and colon cancer.

The terms "lymphoma" and "leukemia" as used herein generally refer to malignant tumors derived from blood and bone marrow cells.

The term "sarcoma" as used herein generally refers to malignant tumors derived from connective tissue, or mesenchymal cells.

The term "mesothelioma" as used herein generally refers to tumors derived from the mesothelial cells lining the peritoneum and the pleura The term "glioma" as used herein generally refers to tumors derived from glia, the most common type of brain cell.

The term "germinoma" as used herein generally refers to tumors derived from germ cells, generally found in the testicle and ovary.

The term "choriocarcinoma" as used herein generally refers to malignant tumors derived from the placenta.

The term "attached," as used herein generally refers to covalent binding, adsorption, and physical immobilization.

The terms "associated with," "binding" and "bound" are identical in meaning to the term "attached."

The term "nanoparticle" as used herein generally refers to a particle, generally metallic, semiconducting, magnetic, ceramic and dielectric, having a diameter in the range of about 1 nm to about 1000 nm.

The terms "polymer" or "biopolymer", as used herein generally refer to a compound having two or more monomer units, and is intended to include linear and branched polymers, and copolymers, the term "branched polymers" encompassing simple branched structures as well as hyperbranched and dendritic polymers. The term "monomer" is used herein to refer to compounds that are not polymeric. "Polymers" or "biopolymers" herein may be naturally occurring, chemically modified, or chemically synthesized.

The term "functional group" generally refers to compounds that may be suitable for chemically binding of a first and second molecule together. chemical bonding may be considered to broadly cover bonding with some covalent character with or without polar bonding and can have properties of ligand-metal bonding along with various degrees of ionic bonding. The functional group may refer to ligand-receptor binding relationships were covalent bonding may not be the typical association. The functional group may be selected based on the composition of the molecule. Another functional group of the linker may be suitable for covalent bonding a first and second molecule together. Covalent bonding refers broadly to covalent bonds with sigma bonds, pi bonds, hydrogen bonds, other delocalized covalent bonds and/or other covalent bonding types, and may be polarized bonds with or without ionic bonding components and the like. Covalent linkers include functionalized organic molecules. The functional groups may include hydroxyl groups, amino groups, carboxyl groups, carboxylic acid anhydride groups, mercapto groups, and hydrosilicon groups.

The invention relates to systems and methods for fabrication of an agent, such as a therapeutic agent or an imaging agent, entrapped or encapsulated in a vehicle, capsule, particle, vector, or carrier in order to maximize treatment and/or imaging of malignancy while minimizing the adverse effects of treatment and/or imaging. Particularly, the systems and methods of the invention may form at least a two-liquid electrified jet, as described in FIG. 1, using a single capillary tube for the production of capsules having entrapped or encapsulated agents. More particularly, the invention provides systems and methods for producing capsules and particles with at least one encapsulated and/or entrapped agents, such as therapeutic agent, imaging agents, and other constituents.

In one embodiment of the invention, the capsules may serve multiple purposes. First, the capsules may protect the encapsulated agent from biological attack and degradation before it reaches the target site. Second, the capsules may prevent surface interaction of the agent from inducing undesired signal pathways and introduce the generation of a cascade of proteins or hormones within the target cells thereby limiting the agents' effectiveness.

The capsule(s) having the entrapped or encapsulated agents may be used for the treatment or imaging of cancer in a patient. For example, the capsule may have an entrapped or encapsulated therapeutic agent for the treatment of malignant cancers such as lymphoma, leukemia, sarcoma, mesothelioma, glioma, germinoma, and choriocarcinoma. furthermore, the capsule may have an entrapped or encapsulated imagining agent for the detection of cancer. The capsule of the invention may also have a combination of entrapped or encapsulated therapeutic agents and imaging agents.

Figure 2:
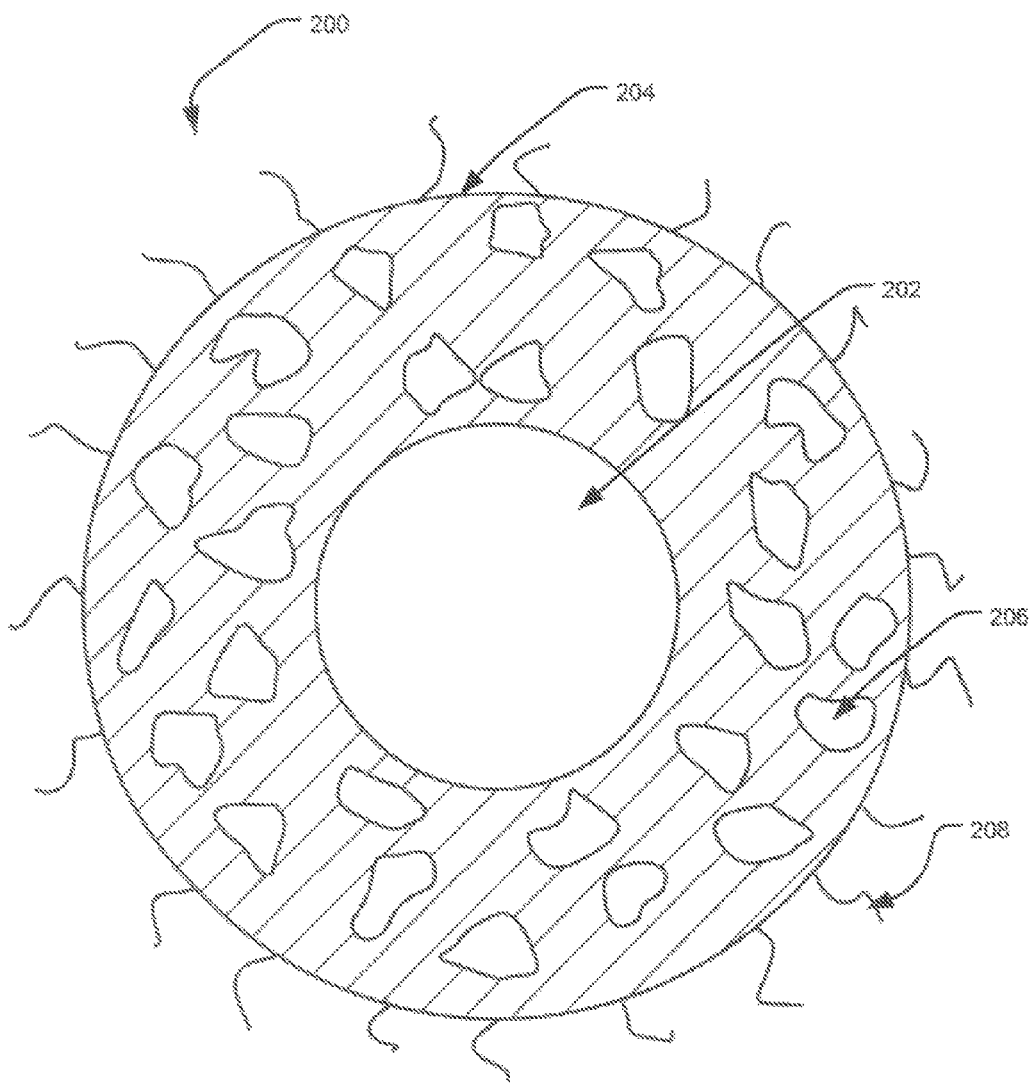
FIG. 2 is a schematic showing the general architecture of a capsule produced by the methods of the invention.

FIG. 2, which illustrates an embodiment of the invention, is a schematic showing the general architecture for a capsule 200 with a distinct core region 202 and shell region 204. The core 202 may contain one or more agents, such as therapeutic agents of biological or abiological origin. the shell may be made from one or more biocompatible polymers and may contain entrapped domains 206 of one or more materials, which may be responsible for the opening of the shell when the vesicle is substantially inclose proximity to or inside the target site, such as malignant cells. Additionally, the capsule 200 may also serve as a contrast agent for imaging purposes. Abiological or functional groups 208 may be chemically or physically grafted onto the surface of the shell 204, which may facilitate transport by receptor or surface charge mediated endocytosis to and/or into the target site, such as malignant cells. Specifically, for example, malignant cells may over-express certain receptors and surface modification of the capsule 200 with functional groups 208 that selectively bind to the over-expressed receptors on the surface of the malignant cells may improve transport of the capsule 200 to and/or into the malignant cells.

There is no requirement that capsule 200 is spherical, other configurations and shapes, such as oblong, tubular, and ellipsoid may also be suitable for use in the invention. Additionally, capsule 200 may be configured as an independent particle or may be configured to be a series of capsules attached to each other in a chain-like fashion. In particular, if capsule 200 is configured in a chain-like series, the capsules may have a length in the range of about 0.03 µm to about 30 µm. Moreover, capsule 200 may be also be effective if it has an oblong shape, tubular shape or ellipsoid shape, if the length such as a minor axis in the case of an ellipsoid, or a diameter in the case of a tube, is sufficiently small to allow passage through the target site, such as a malignant cell membrane. The diameter or minor axis of the capsule may be in a range of about 10 nm to about 1 µm.

According to one embodiment of the invention, the architecture of the capsule may be based upon the mass ratio of shell material to core material and the composition and mass of the agents such as therapeutic agents, imaging agents, and other constituents, for example. Furthermore, the distinct core and shell regions may not be required. One or more agents, such as therapeutic or imaging agents may be entrapped and/or dispersed inside particles having at least one biocompatible substance such as a biopolymer. The capsule may include other additives, such as, a chemically functionalized surface to exploit receptor biochemistry properties of malignant cells, dispersed particles that may aid in the breaking or segregation of the therapeutic and/or an imaging agent carrying capsules once the capsules are substantially proximate to or inside the malignant cells.

According to an embodiment of the invention, the capsule may have a shell thickness in the range of about 10 nm to about 10 µm, and more particularly, in a range of about 20 nm to about 150 nm. In particular, the capsule shell has a thickness of about 20 nm. Moreover, the capsule may have a size in the range of about 25 nm to about 25 µm, and more particularly, in a range of about 50 nm to about 500 nm. Specifically, the capsule has a size of about 250 nm.

In another embodiment, the capsule including at least one agent, such as a therapeutic agent or an imaging agent, may be transported into the target cells by processes such as endocytosis, transformation, or transduction. Once the capsule enters the target cell, the action of the therapeutic agent for treatment may be induced by chemical stress or external radiation. Once activated, the therapeutic agent may induce the desired effect, such as apoptosis of the target cells. The therapeutic agents may be genetic material such as nucleic acid, RNA, DNA, bacteria, viruses, proteins, nucleic acid fragments, nucleic acid encoding a gene product, and abiological agents. Examples of the imaging agents may include magnetic particles, photonic sensitive materials, radioactive isotopes, and contrasting agents.

The capsule of the invention may have magnetic nanoparticles of low toxicity dispersed in it for external magnetic guidance of the capsule. In particular, the magnetic nanoparticles may include ferromagnetic materials, such as metallic iron and certain metal oxides such a transition metal oxide, and rare earth based magnetic materials. Specifically, the magnetic nanoparticle may be a magnetite, such as $Fe_3O_4$ having a size in the range of about 1 nm to about 300 nm, and specifically, a size of about 10 nm. In addition to magnetic nanoparticles, other materials may be dispersed within the capsule such as materials sensitive to light or electric fields such as metallic silver or gold, which may be used for imaging effects. Moreover, the metallic silver or gold may be used in combination with radioactive emitters such as beta, gamma, or alpha emitters for imagining effects.

Figure 3:
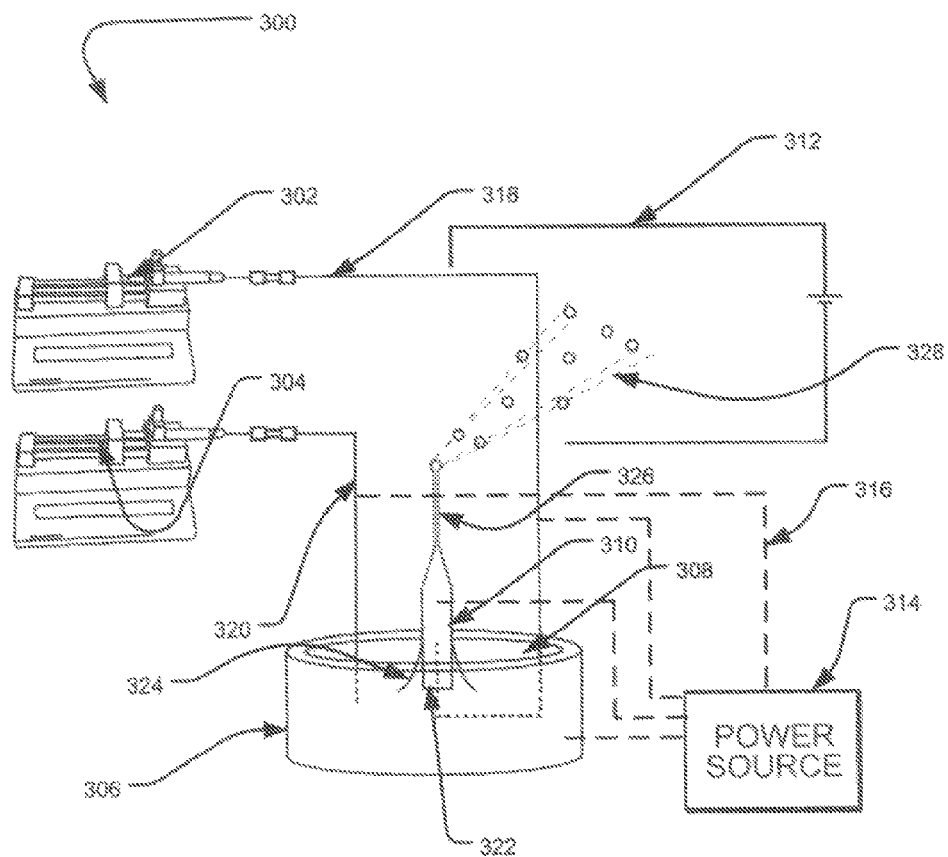
FIG. 3 is a schematic showing an upward flow electrohydrodynamic system, according to principles of the invention.

Referring to FIG. 3, which illustrates an embodiment of the invention, an upward flow EHD system 300 is shown for forming at least a two-fluid electrified jet (FIG. 1) by using a single capillary tube. Here, system 300 may include syringe pump 302 containing a core fluid, syringe pump 304 containing a shell fluid, a fluid bath 306 containing shell fluid 308, tube 310, collection plate 312, voltage source 314, electrode 316, core fluid supply tube 318, shell fluid supply tube 320, open end 322 of tube 310, fluid flow of shell fluid 324, collection zone 326, and plume 328. As depicted in FIG. 3, syringe pump 302 containing the core fluid supplies the core fluid via supply tube 318 to tube 310 which delivers the core fluid upwards from its open end 322, while the shell fluid 308 is delivered via wetting and capillary forces from the fluid bath 306 surrounding the tube 310. The fluid flow of the shell fluid is designated as numeral 324. The electrode 316 may placed in several locations, such as on tube 310, in fluid bath 306, the core fluid supply tube 318, or the shell fluid supply tube 320, for example. the electric potential of the core fluid and the electric potential of the shell fluid may be the same.

The process throughput may be increased by making a device including more than one tube operating as tube 310, as described below. Depending on the physical and chemical properties of the shell fluid 308 and the core fluid delivered through tube 310, the height difference between the open end 322 of tube 310 and the surface of shell fluid 308 in the fluid bath 306, the ratio of core and shell fluids in the upwards traveling electrified liquid jet may be varied.

Moreover, in a further embodiment, a collector electrode 312 may be placed above the surface of shell fluid 308 in fluid bath 306 in a variety of orientations. For example, if a flat metal surface is used as collector electrode 312, the surface of the collector electrode may be oriented parallel or non-parallel to the surface of shell fluid 308 in fluid bath 306, or a different type of collector electrode configuration may be selected, such as a rotating drum.

The plume 328 may contain same-charge droplets that repel each other and thus, travel toward collector electrode 312 with an ever-increasing cross-sectional area. The electric potential of the core fluid and the electric potential of the shell fluid may be the same, due to their intimate electrical contact. The electrical potential and the voltage are related quantities. The electrical potential may depend upon the separation between the point at which a cone-jet region is formed, such as region 326, and electrode collection plate 312. The separation may have a distance in a range of about 1.5 inches to about 15 inches. Moreover, the applied voltage nay be in a range of about 0.5 kV to about 35 kV.

Figure 4:
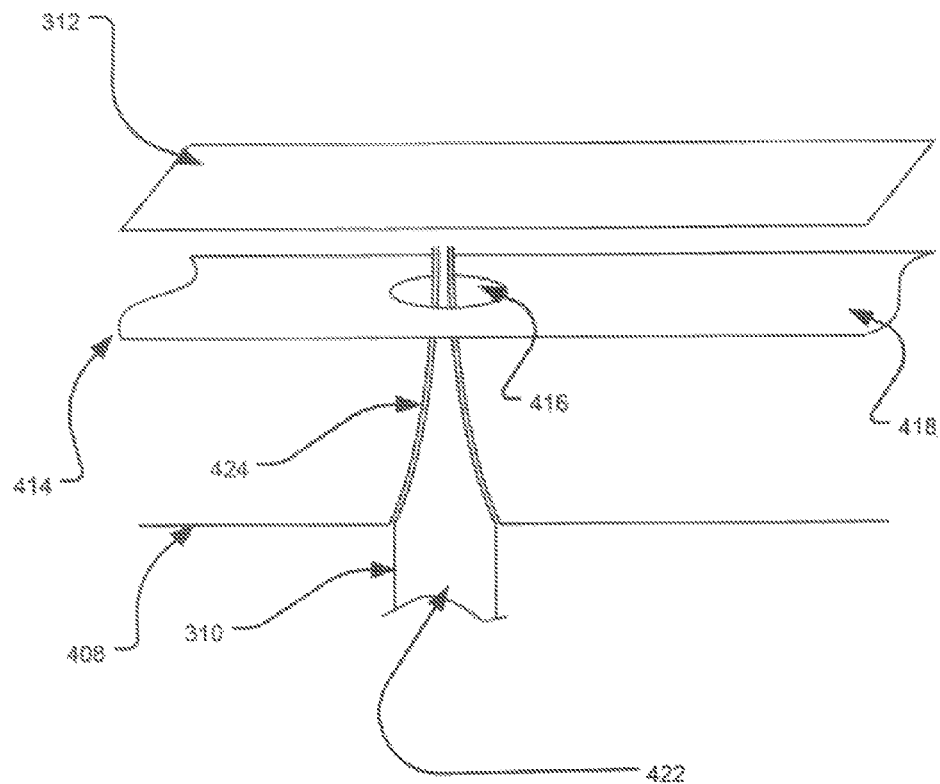
FIG. 4 is a blow-up schematic of the upward flow electrohydrodynamic system of FIG. 3, showing the addition of the extractor.

Turning to FIG. 4, which illustrated another embodiment of the invention. shell fluid 408, tube 310, collection plate 12, shell fluid flow 434, and an extractor 414 are shown. the extractor 414, which is an intermediate electrode, may be incorporated to aid in the formation of the two-fluid electrified jet. The extractor 414 may be an orifice 416 made on a conductive body 418 and may be placed at a short distance from the open end 422 of tube 310. The extractor body may be biased at an intermediate electrical potential between those of tube 310 and the collection plate 312.

In an alternate embodiment, the direction that the electrified two-fluid ejected need not be upwards. Similar wetting by capillary forces of tubes or conduits delivering the core fluid may be effected to produce downward flows of the two-liquid electrified fluid jets. Electrified fluid or solids structures may be made to undergo total or partial electrical discharge at a region after the extractor. This configuration may increase the time of travel of the fluid or solid structures from the region where the electrified meniscus or menisci are formed, to the collection zone, because a smaller electrical charge means decreased mobility. The totally or partially discharged fluid or solid structures may be transported to a collection zone via use of gas flows.

Figure 5:
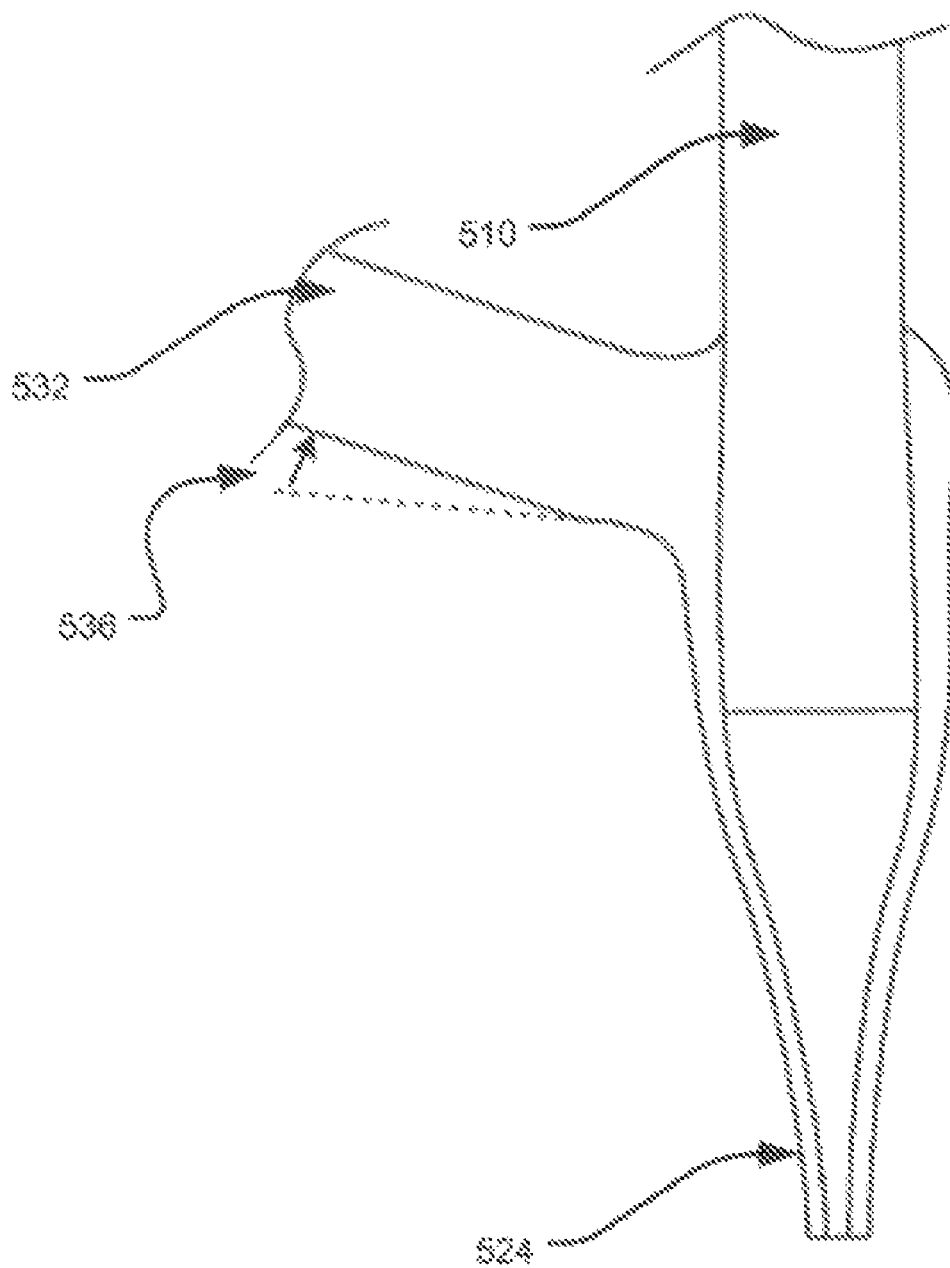
FIG. 5 is a schematic showing a downward flow electrohydrodynamic system using a single capillary tube to form a two-fluid electrified jet, according to principles of the invention.

The concept of wetting the external wall of a tube or conduit used to deliver the core fluid for a two-liquid electrified fluid jet may adopt other configurations. Referring to FIG. 5. which illustrates an embodiment of the invention, a tube 510 used to deliver the core fluid, a second tube 532 used to deliver the shell fluid, and the shell fluid flow 524 is shown. Besides flow rates, electric field strength and other variables considerations, the distance between the outer wall of tube 510, the open end of tube 532, and the angle 536 may be adjusted to ensure adequate wetting the outer wall of tube 510 for formation of a desired two-fluid electrified menisci and electrified two-fluid jet. Adding two or more tubes or conduits serving as tube 532 to deliver the shell fluid may be considered a natural extension of the system illustrated in FIG. 5. flow rates for both the core and the shell fluids may be forced by the action of gravity i.e., by placing their respective supply reservoirs at an elevated distance with respect to the region where the electrified two-fluid meniscus is formed, by the action of mechanical or digital pumps, or driven by magnetic fields if one or both fluids are magnetic. Once angle 536 and the number of tubes or conduits serving the purpose of tube 532 may be taken as trivial degrees of freedom to produce two-fluid electrified liquid jets, a number of other natural extensions to FIG. 5 may be realized.

Figure 6A:
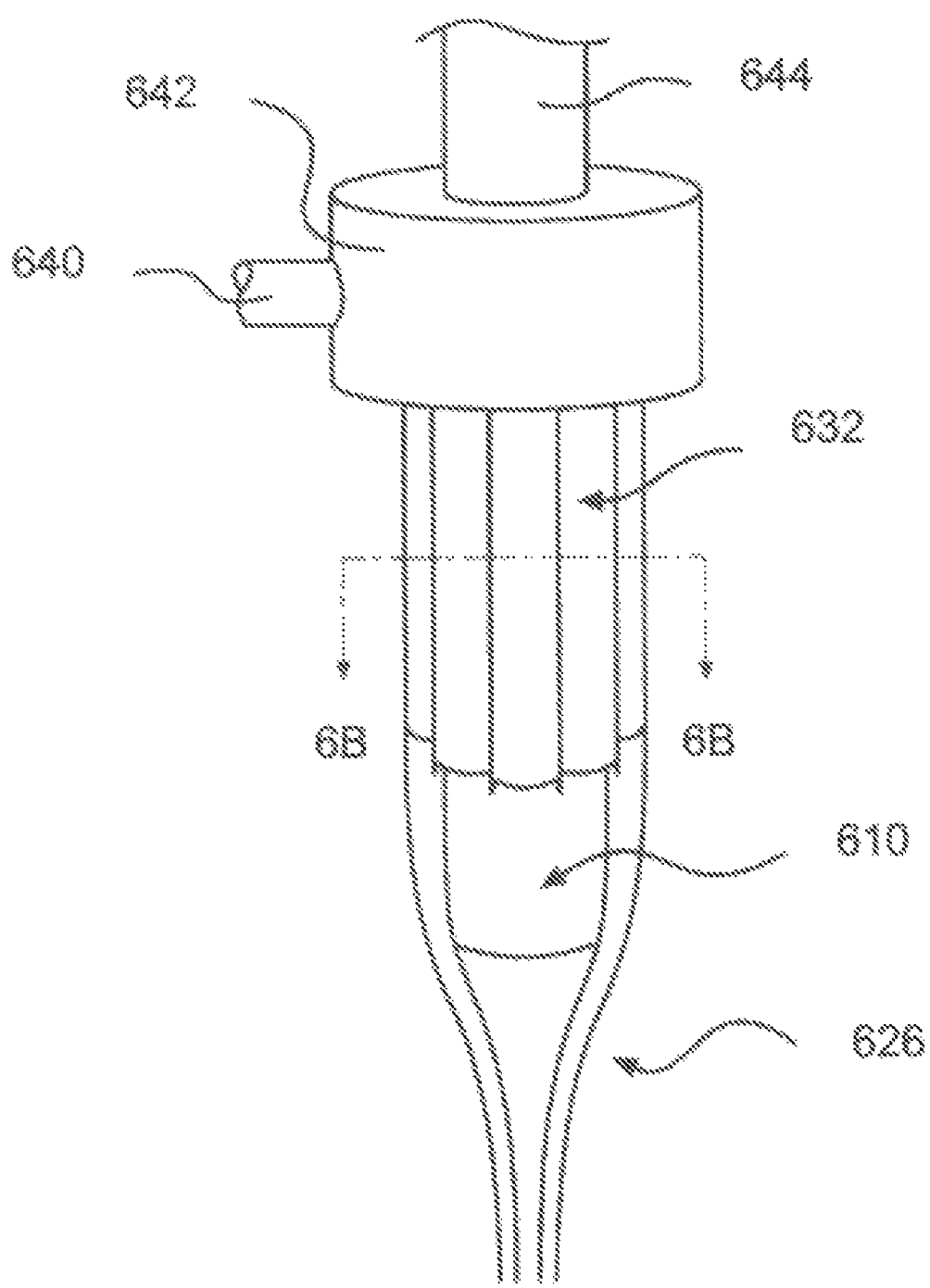
FIG. 6A is a schematic depicting a downward flow electrohydrodynamic system using a plurality of tubes or conduits to deliver the shell fluid, according to principles of the invention.

For example, FIG. 6, which illustrates another embodiment of the invention, shows one such natural extension to the principles in FIG. 5. In FIG. 6A, eight tubes or conduits 632 may be used to deliver the shell fluid. Tubes 632 may be oriented at an angles of about 90 degrees, when the angle is defined in the same way as angle 536 in FIG. 5 is defined. Tube 610 delivers the core fluid, which is supplied by the core fluid inlet 644, and an electrified, two-fluid meniscus is formed when both the shell and the core fluids are accelerated by the action of an electric field gradient toward a collection zone 626, or collector electrode, as previously describe. In FIG. 6A, a shell fluid inlet port 640 may be used to feed the shell fluid first into an encasement 642 that envelops tube 610, and then through tubes 632. The number of tubes 632 to be used may be based on factors such as, but not limited to, the physical and chemical properties of the shell and core fluids, and the operating variables, such as, but not limited to, the flow rates of the core and shell fluids, and the electric field strength and its spatial distribution. The distance between the open ends of tubes 610 and the open end of tube 632, and the cross sectional areas of tubes 610 and tube 632, as shown in FIG. 6B, may also be determined based on operating variables, and the physical and chemical properties of the involved fluids. Tubes 632 need not be in contact with each other.

Figure 7A:
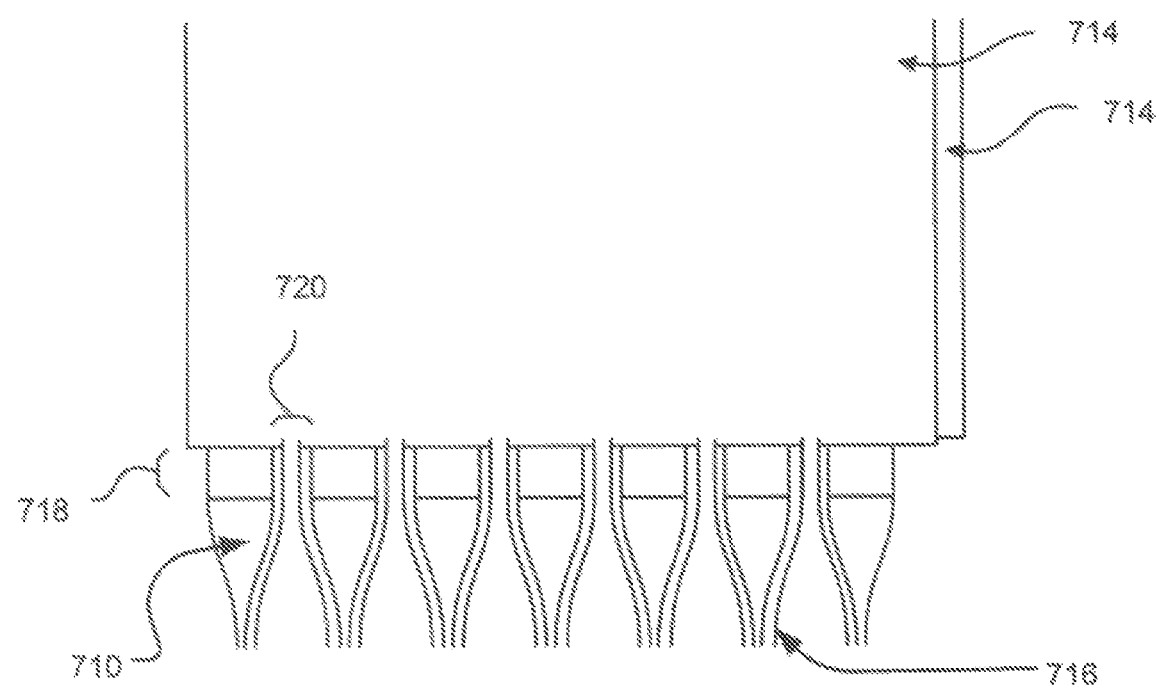
FIG. 7A is a schematic showing a downward flow electrohydrodynamic system using a plurality of capillary tubes positioned between two plates to deliver the core fluid, according to principles of the invention.
Figure 7B:
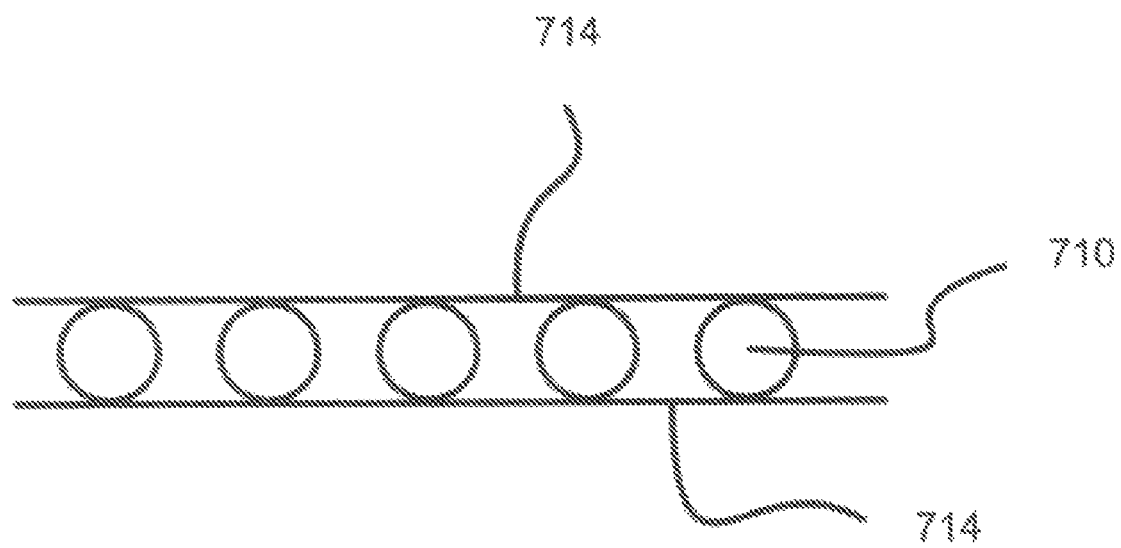
FIG. 7B is a cross-section of FIG. 7A.

In another embodiment, the concept of wetting the tube or conduit delivering the core fluid may be extended to other practical configurations. FIG. 7A, which illustrates an embodiment of the invention, shows a configuration, where the number of tubes 710 may be used to deliver the core liquid from their open ends. Tubes 710 may be sandwiched between two walls 714. The shell fluid 716 may then be delivered through the space between adjacent tubes 710 (FIG. 7B provides the cross section of FIG. 7A). By the action of an applied electric field, electrified, two-fluid menisci and jets may be created.

Moreover, gap 718 and gap 720 may be adjusted or designed based upon operating variables such as, but not limited to, flow rates of the two fluids involved and the electric field strength and its spatial distribution. In particular, the close electrified menisci are packed i.e., the smaller gap 720 is made, the higher the electric field required for forming the menisci. Unless the gas environment surrounding the electrified menisci is not air, corona discharges may occur, and these may compromise process continuity. Thus, a person of skill in the art would determine gap 720 based on these principles, on knowledge of the physical and chemical properties of the core and shell fluids, and the process variables. For example, if the physical and chemical properties of the core and shell fluids and the values of the operating variable require gap 720 to be long enough to cause dripping of the shell fluid in between adjacent tubes 710, flow deflectors or baffles may be incorporated between adjacent tubes 710 to convey the outer fluid towards tubes 710. Gap 718 may be determined by the wetting phenomena occurring between the outer walls of tubes 710 and the shell fluid 716. Additionally, an extractor electrode orifice may be placed at a short distance away from the corresponding two-fluid electrified meniscus, as described above, and may be used to facilitate formation of two-fluid electrified structures.

Figure 8B:
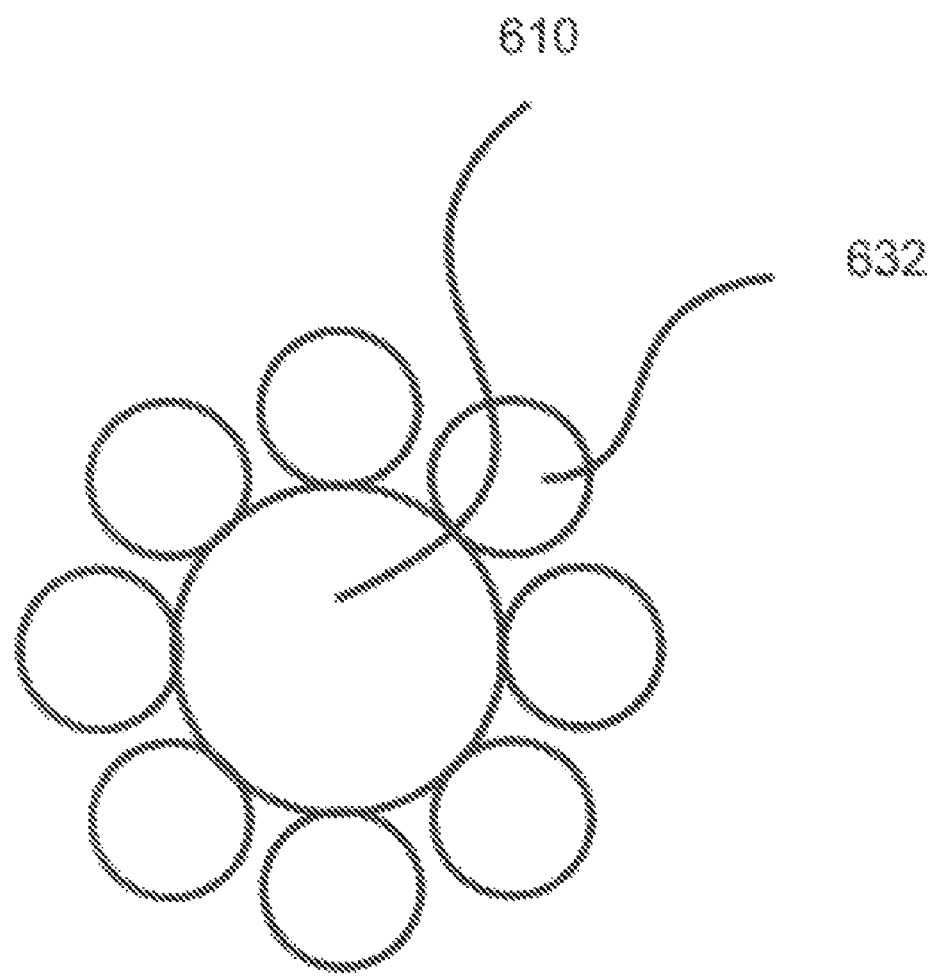
FIG. 8B is a cross-section of FIG. 8A.
Figure 8A:
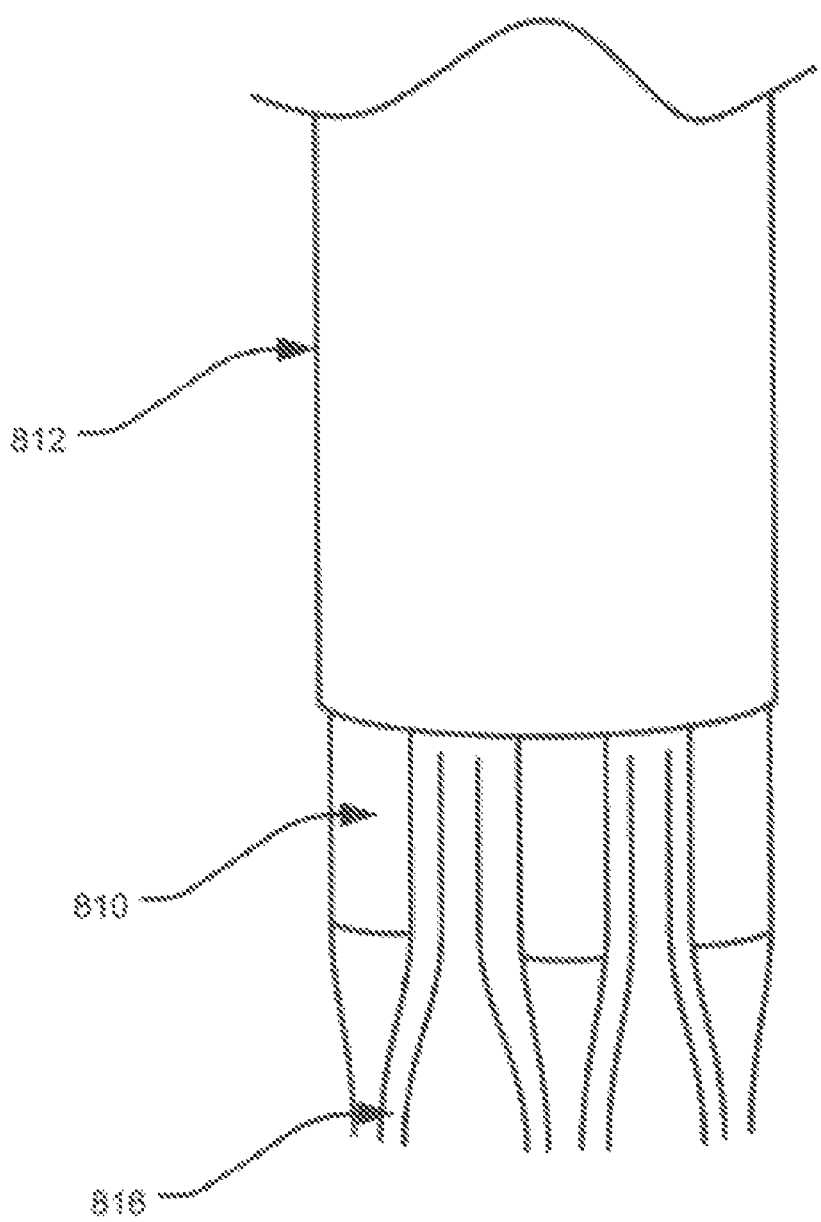
FIG. 8A is a schematic showing a downward flow electrohydrodynamic system using a plurality of capillary tubes to deliver the core fluid, according to principles of the invention.
Figure 8B:
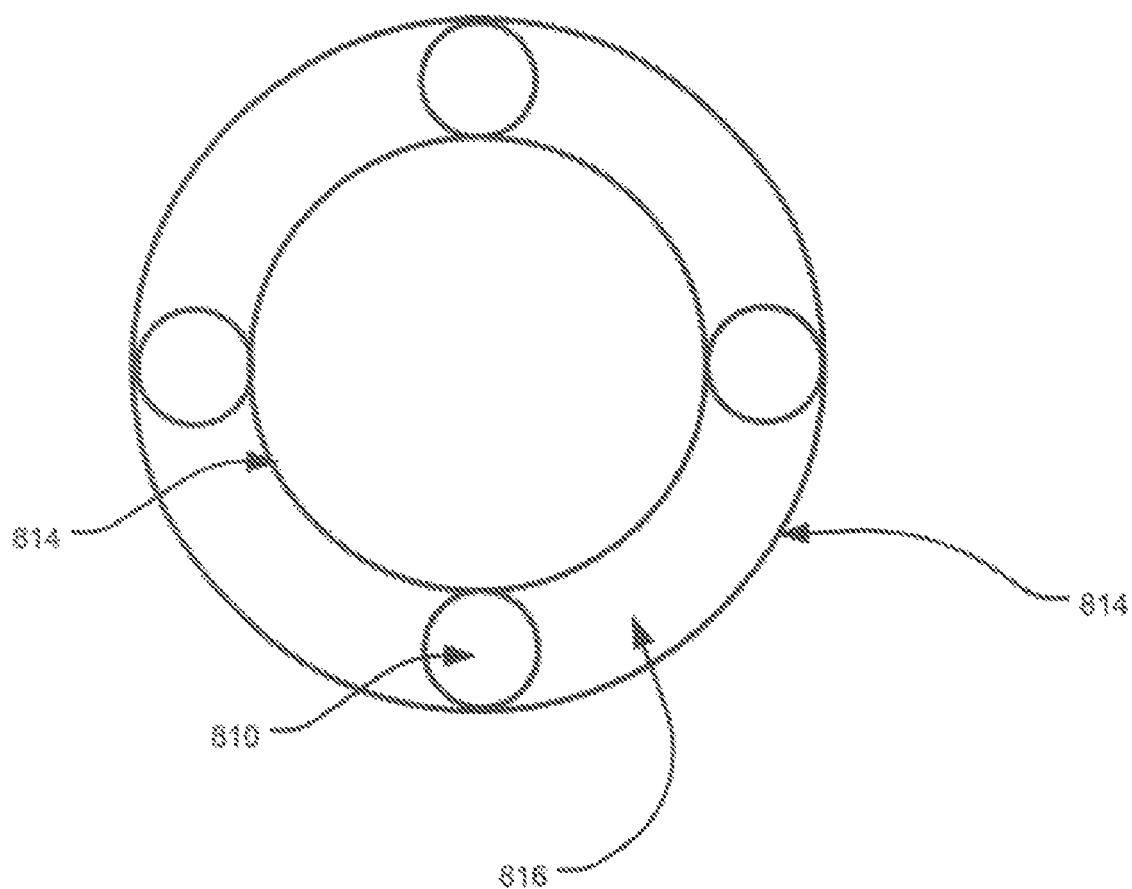

Referring to FIG. 8A, which illustrates an embodiment of the invention, shows that alignment of tubes 810 delivering the core fluid may differ from the alignment shown in FIGS. 7A-7B. As shown in FIG. 8A-8B, tubes 810 may be sandwiched between a cylindrical encasement 812 and a rod 814, and shell fluid 816 may be delivered though the space between adjacent tubes 810. The number of tubes delivering the core fluid in FIGS. 7A-7B and FIGS. 8A-8B may be determined based on the desired process throughput. Likewise, the inner diameters of the tubes delivering the core fluid 810 may be in the range of about 0.05 mm to about 2.0 mm. The diameter of tubes 810 may also be based on the properties of the involved fluids and the chosen operating variables such as, but not limited to, the electric filed strength and its spatial distribution, and flow rates. The cross sectional areas of the tubes delivering the core liquid 810 need not be circular, as other shapes such as, but not limited to, ellipsoidal and polygonal can produce electrified twp-fluid menisci and jets, and the open, cross sectional area of the tube need not be oriented perpendicular to the axis of the tube. The open end of the tube may adopt other shapes such as, but not limited to, conical or beveled.

Packing side-by-side a plurality of the fixture shown in FIGS. 7A-7B to increase product throughput may be desired to take advantage of the general principle of wetting the outer wall of a conduit or tube delivering the core fluid with the shell-forming fluid. Likewise, the principles of operation of the device shown in FIGS. 8A-8B may be used to sandwich more than one circular layer of tubes or conduits delivering the core fluid between cylindrical encasements. FIGS. 7A-7B and FIGS. 8A-8B are thus not limiting, as the surfaces that may be used to sandwich a plurality of tubes delivering the core fluid need not be cylindrical or flat, since other surfaces with regular or irregular shapes may be used by the person skilled in the art.

Figure 9:
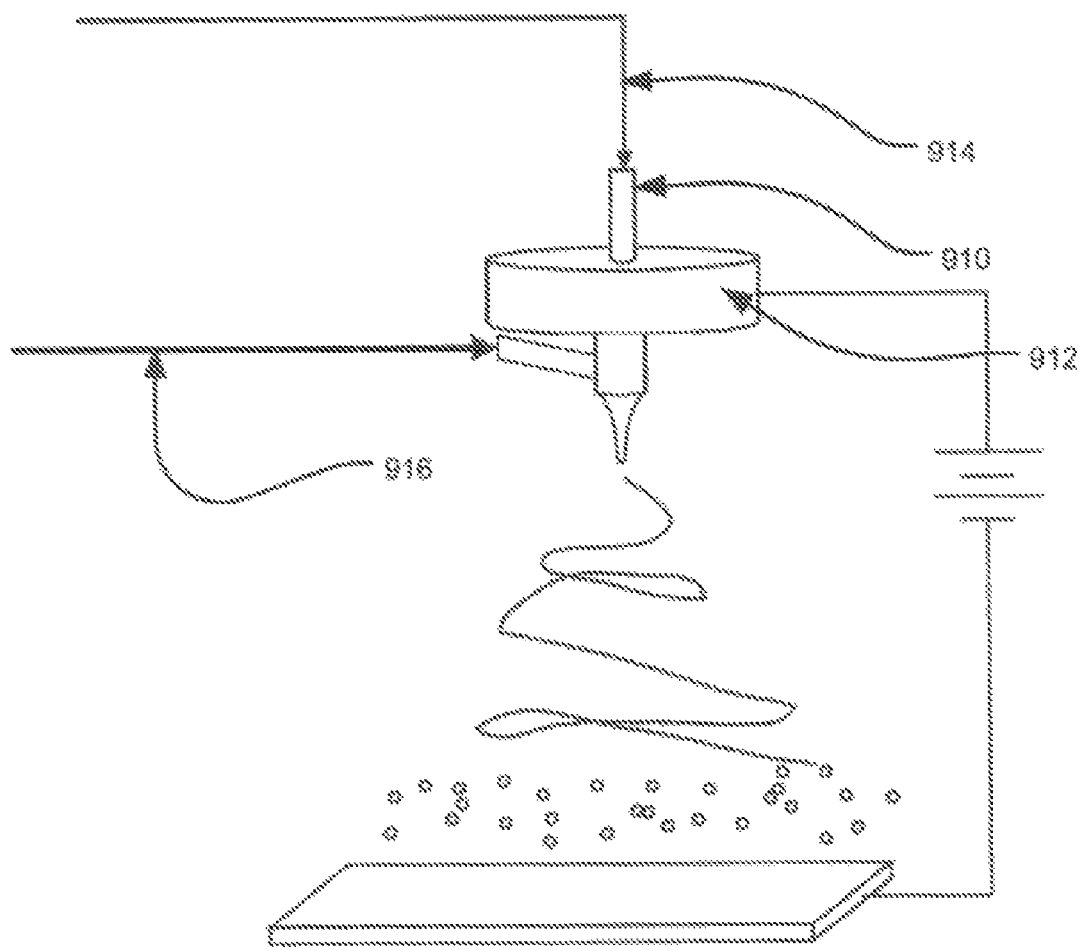
FIG. 9 is a schematic showing a downward flow electrohydrodynamic system used to produce a capsule having at least three layers, according to principles of the invention.

In one embodiment of the invention, the concept of wetting the outer wall of a tube or conduit delivering fluids by the action forced flow and electric fields can be extended to produce multi-fluid electrified menisci and jets. Referring FIG. 9, which illustrates and embodiment of the invention, shows the use of an arrangement comprising two coaxial tubes 910 and 916 to deliver core fluid 914 and shell fluid 912, and a third tube or conduit 916 used to deliver a third fluid. There are natural extensions of the principle of creating an enveloping stream of a third fluid via wetting of the external wall of the outer tube or conduit of the two-tube coaxial arrangement. By way of example, more than two tubes with cylindrical cross sections may be arranged in a coaxial manner, to deliver more than two fluids via forced flows and electric fields. Thus, if N is the number of such coaxial cylindrical tubes, (N+1) fluids can be delivered by wetting the outer wall of the outermost cylindrical tube of the coaxial arrangement of N tubes, and by the action of forced flows and electric fields, to form an electrified (N+1)-fluids meniscus and jet or jets.

Figure 10:
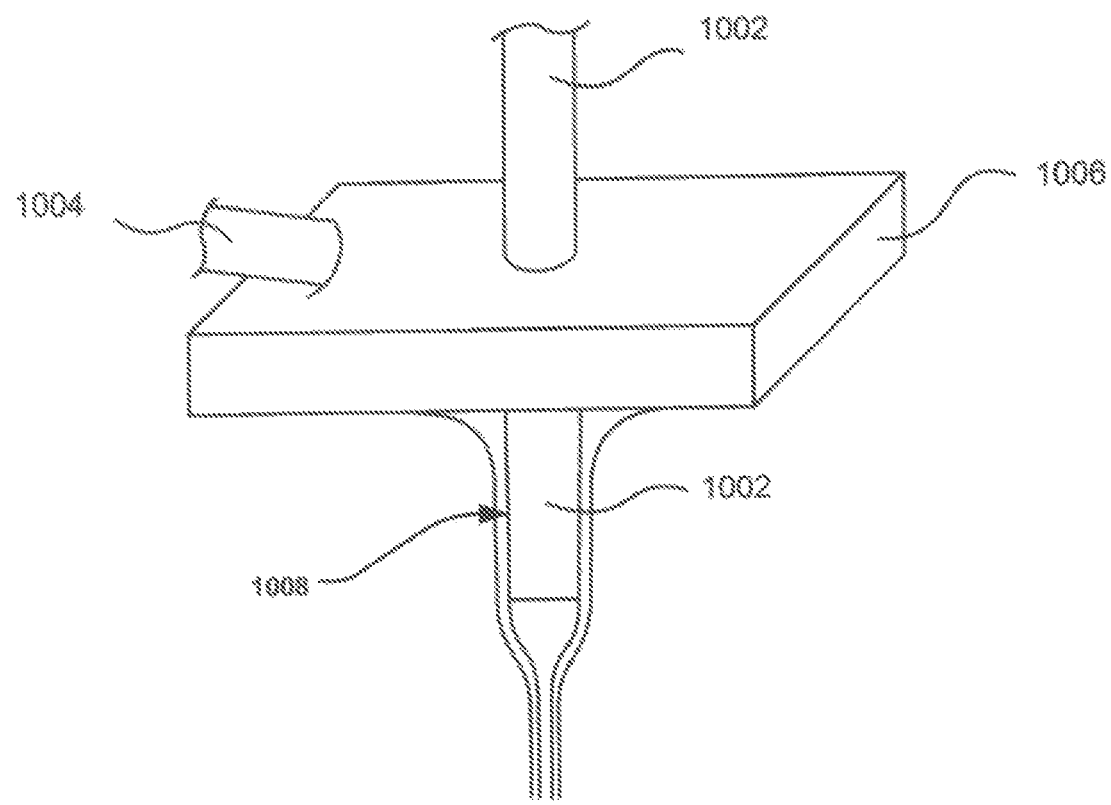
FIG. 10 is a schematic showing a downward flow electrohydrodynamic system using a porous body to deliver the shell fluid to produce the two-fluid Taylor cone, according to principles of the invention.

FIG. 10, which illustrates yet another embodiment of the invention, depicts wetting the external walls of tubes or conduits carrying the core fluid with the shell fluid. Tube 1002 carries the core fluid. Tube 1004 feeds the shell fluid into the porous body 1006. Porous body 1006 delivers the shell fluid via wetting of the external wall of tube 1002. A volume of the porous body 1006 may be made to envelop tube 1002, and to contact tube 1002 at a fraction of its external wall 1008. The choice of the porous material 1006 may be dictated by the physical and chemical properties of the shell fluid. As one example, a latex sponge may constitute a suitable material to handle shell fluids comprising water and other dissolved or suspended ingredients. The type of porous body 1006 and the pore size distribution of porous body 1006 may be based on the desired flow rates of the core and shell fluids, and they physical and chemicals properties of the shell fluid. Examples of porous materials may include silicone based polymers, polyamide based cross-linked polymers, melamine-formaldehyde based polymers, liquid paraffin, polyvinyl alcohol polymers, and poly(l-lactide) acid.

Moreover, a fixture comprising an arrangement of a plurality of tubes or conduits 1002 may be employed. The cross sectional areas of the tubes 1002 delivering the core liquid need not be circular, as other shapes such as, but not limited to, ellipsoidal and polygonal, may produce electrified two-fluid menisci and jets, and the open, cross sectional area of the tube need not be oriented perpendicular to the axis of the tube. The open end of the tube may adopt other shapes such as, but not limited to, conical or beveled. Tube 1002 may be substituted by a multi-tube arrangement consisting of more than one tube with cylindrical cross arranged in a coaxial manner, as described above, to deliver more than two fluids via forced flows and electric fields. The concept of placing an extractor electrode orifice at a short distance away from the corresponding electrified fluids meniscus, as described above, may be used expand the system illustrated in FIG. 10 and to facilitate formation of multi-fluid electrified structures.

Figure 11:
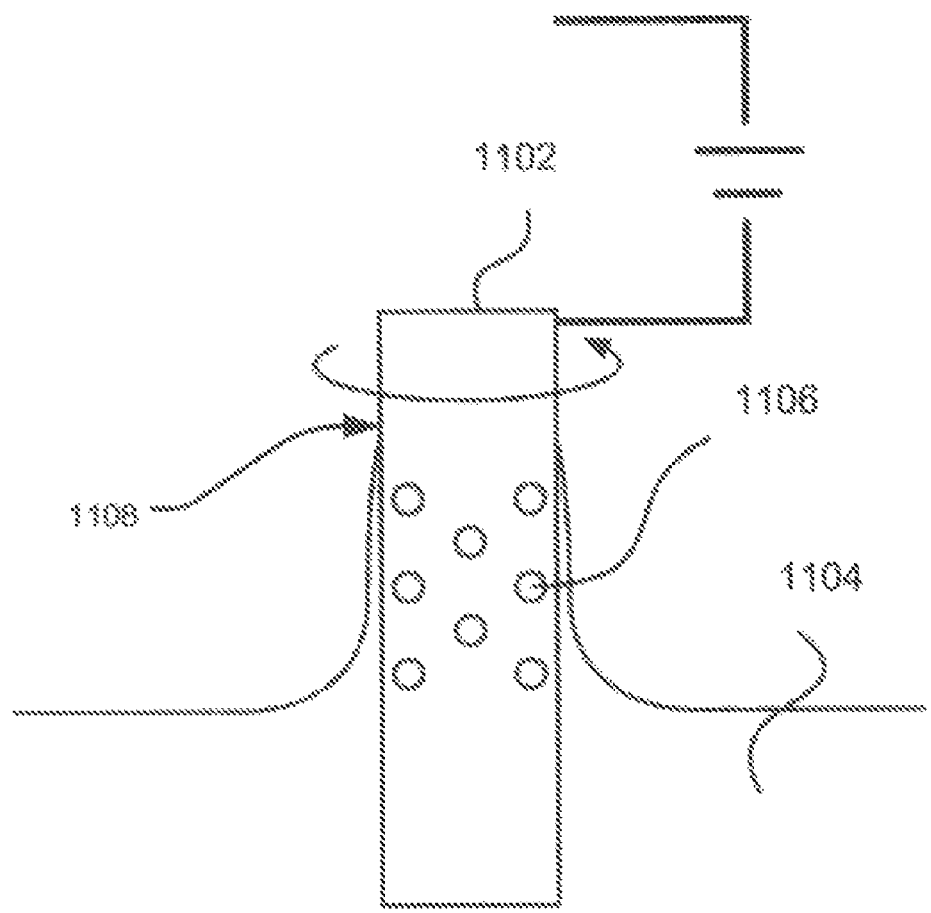
FIG. 11 is a schematic of an upward flow electrohydrodynamic system where the core fluid reservoir may rotate, according to principles of the invention.

Turning to FIG. 11, which illustrates another embodiment of the invention, the delivery of the shell fluid via wetting phenomena is depicted. A reservoir 1102 for the core fluid may rotate by means of any mechanical device (not shown) while partially immersed in a bath 1104 of the shell fluid. the shell fluid may wet the external wall 1108 of the reservoir having the core fluid by the action of capillary forces and other physical phenomena. In the zone where shell fluid wetting of the external wall of reservoir 1102 occurs, at least one of orifices 1105, capillaries protruding the external wall of reservoir 1102, or other conduit shapes may be made on the external wall 1108 of reservoir 1102 to deliver the core fluid through the shell fluid film when an electric field is applied between reservoir 1102 and a collection zone or collector electrode. The distance between adjacent orifices 1106, capillaries or conduit shapes, as well as the rotational speed of reservoir 1102, type of reservoir 1102 material, size and shape, immersion dept of reservoir 1102 into bath 1104, the number and size of orifices 1106, capillaries or conduit shapes, may be based on the physical and chemical properties of the core and shell fluids and the operating variables such as, but not limited to, applied voltage between reservoir 1102 and a collection zone or collector electrode.

In one embodiment, once a two-fluid electrified liquid jet is formed by the methodology of the invention, a variety of fluids may be processed into different shapes such as, but not limited to, hollow fibers and capsules. A family of chemical synthesis methods known as sol-gel may be used to produce such structures from a two-fluid electrified jet. For example, one way of making structures with defined core and shell regions of different composition, requires that the shell fluid undergo total or partial solvent evaporation during the time of travel from ejection of the two-fluid electrified jet from the two-fluid electrified meniscus to the collector electrode or collection zone. The precursor for the solid shell may remain in solution until a critical fraction of solvent evaporates to the surroundings. The core fluid, depending on how it is formulated by the skilled person, may or may not yield a solid phase on collection at the collection zone.

The methodology of the invention may be employed to produce structures with defined core and shell regions from a wide variety of fluids with different chemical compositions. Additional functions such as, but not limited to, magnetic properties may be added to the core or the shell fluids, or both, by formulating the chemistry of the said fluids.

For example, the shells of capsules containing a core fluid with dissolved protein may be made magnetic by suspending magnetite particles in the range of about 100 nm to about 1 nm in the shell fluid precursor prior to processing using the methods described herein. The core fluid and the shell fluid chemistry may be formulated in such a way that neither the core fluid not the shell fluid undergoes solidification before entering the droplet-in-droplet regime depicted in FIG. 3. Once in the droplet-in-droplet regime, a critical amount of slvent evaporation in the shell fluid is achieved, and capsules with a solid shell and a fluid core are collected in the collector electrode.

A variety of proteins, DNA material, cells and other biologically originated matter may be encapsulated using the methodology of the invention. In particular, enzymes are a class of proteins that may serve as biocatalysts, and may be encapsulated in fluid cores such as, but not limited to, pH buffered aqueous solutions, and the shells may be formed from sol-gel precursors having suspended magnetite particles. the magnetite mass fraction in the shell may permit magnetic transport of the capsules once suspended in fluid media. The capsules containing the encapsulated enzymes may be suspended in a fluid containing reactants and products for a reaction catalyzed by the encapsulated enzyme. If the shell is designed with pores large enough to allow diffusion through it of reactants and products for the reaction catalyzed by the encapsulated enzyme, but not as large so as to permit the enzyme to diffuse out of the capsule, it is possible to recover the encapsulated enzyme with the aid of magnetic forces after the desired extent of reaction has been achieved.

For example, in one embodiment of the invention, silicon alkoxide sol-gel chemistry may produce pores in the capsules in the range of about 0.5 nm to about 2.0 nm when controlled, which may be sufficient to allow diffusion of many commercially important reactants and products, but not to allow, for example, about a 50 kDa to about a 60 kDa transaminase enzyme to escape out of the sol-gel derived shell. A natural extension of this concept is to design core fluid formulations containing substances of biological origin other than proteins such as, but not limited to DNA, DNA fragments, genes, and cells.

Figure 12:
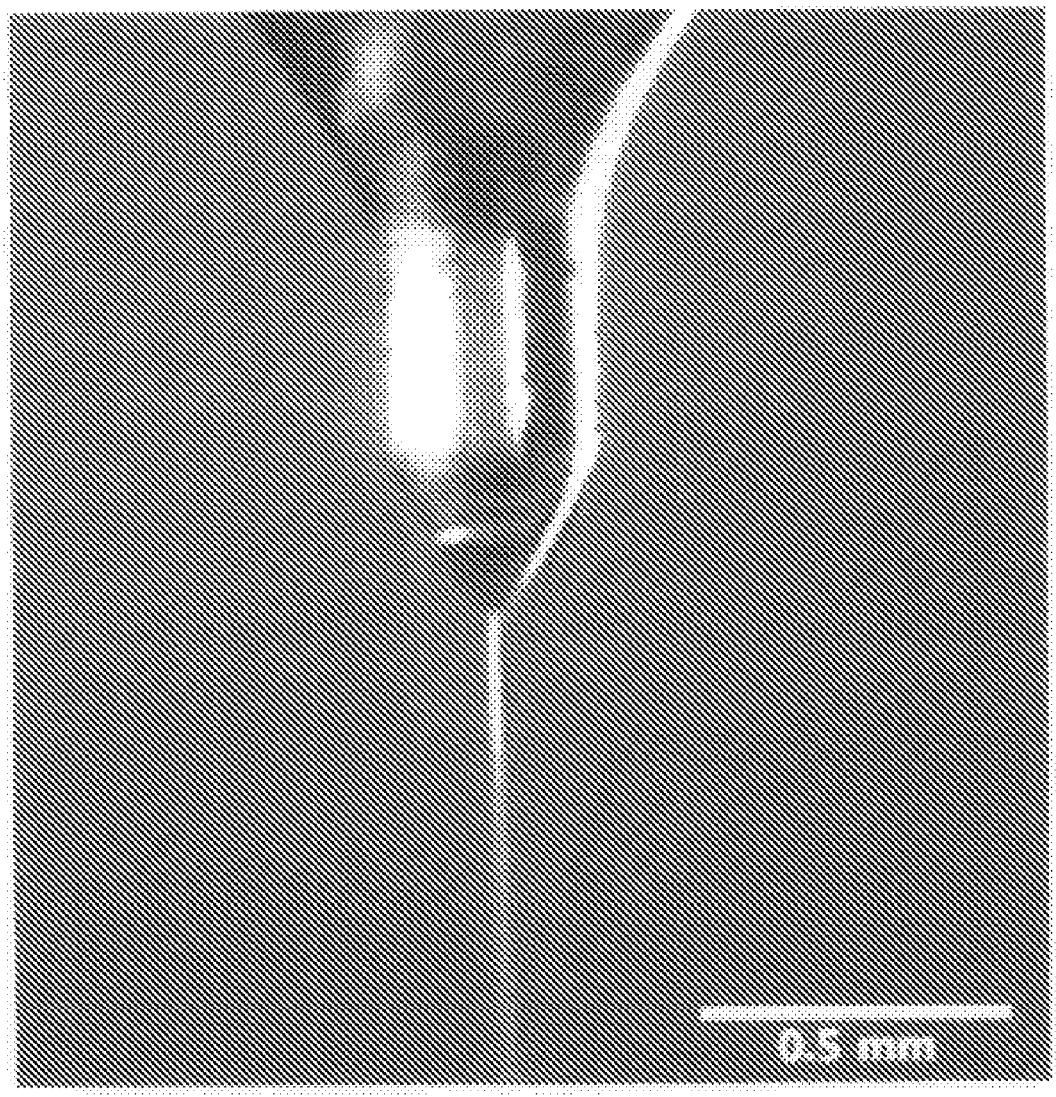
FIG. 12 is a photograph of the electrified meniscus formed under an electric field and forced flow of the shell formulation.

According to one embodiment, a magnetite nano-particle formulation compatible with the silicon alkoxides based shell chemistry may yield magnetite may be coated with a silicon alkoxide layer having a size in the range of about 2 nm to about 4 nm. such a silicon alkoxide layer makes it ideal for firmly anchoring the magnetite to the shell solid phase via cross-linking sol-gel processes. A specific mass fraction of magnetite phase in the shell is in the range of about 0.1 to about 0.8. FIG. 12 is a photograph of the electrified liquid meniscus formed under an electric field and forced flow of the shell formulation that had magnetite particles added.

In another embodiment of the invention, the capsule suitable for the treatment and/or imagining of malignant cancers may be fabricated by employing electrospray. In general, the electrospray methodology may include delivering a liquid containing the encapsulate(s) through a single nozzle, capillary, conduit, or orifice, applying an electrical potential between the nozzle and a collection region (herein after "counter-electrode"), forming a DC electrospray of the liquid containing the encapsulate (s), accelerating the DC electrospray towards the counter-electrode, forming the shell enveloping the DC electrospray from its delivery region to the counter-electrode through a reaction between a suitable shell-forming monomer with liquid components in the electrospray. The shell-forming monomer and the liquid components do not compromise the integrity and function of the encapsulate(s). The capsules may be collected on the counter-electrode are collected for storage and use.

Figure 13A:
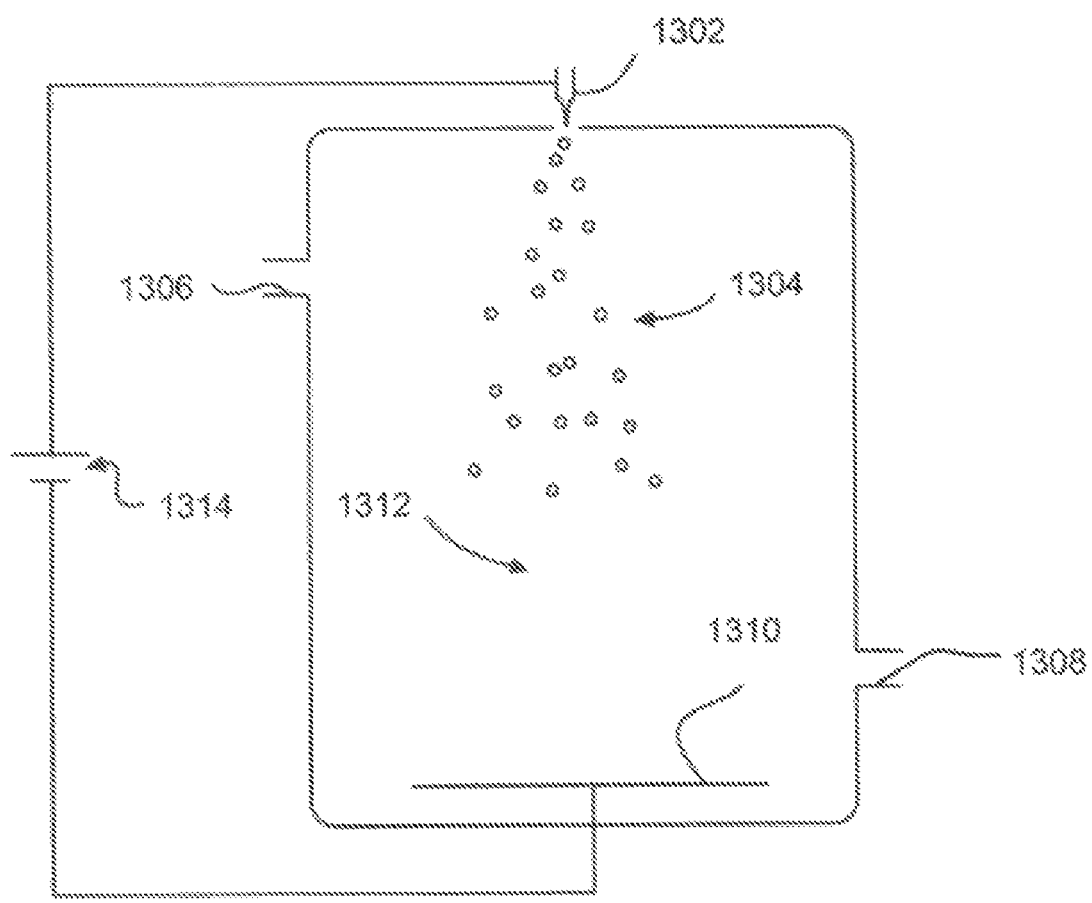
FIG. 13A is a schematic depicting a method of the invention based on a combination of chemical reactions between the electrospray and its surrounding gas phase, according to principles of the invention.
Figure 13B:
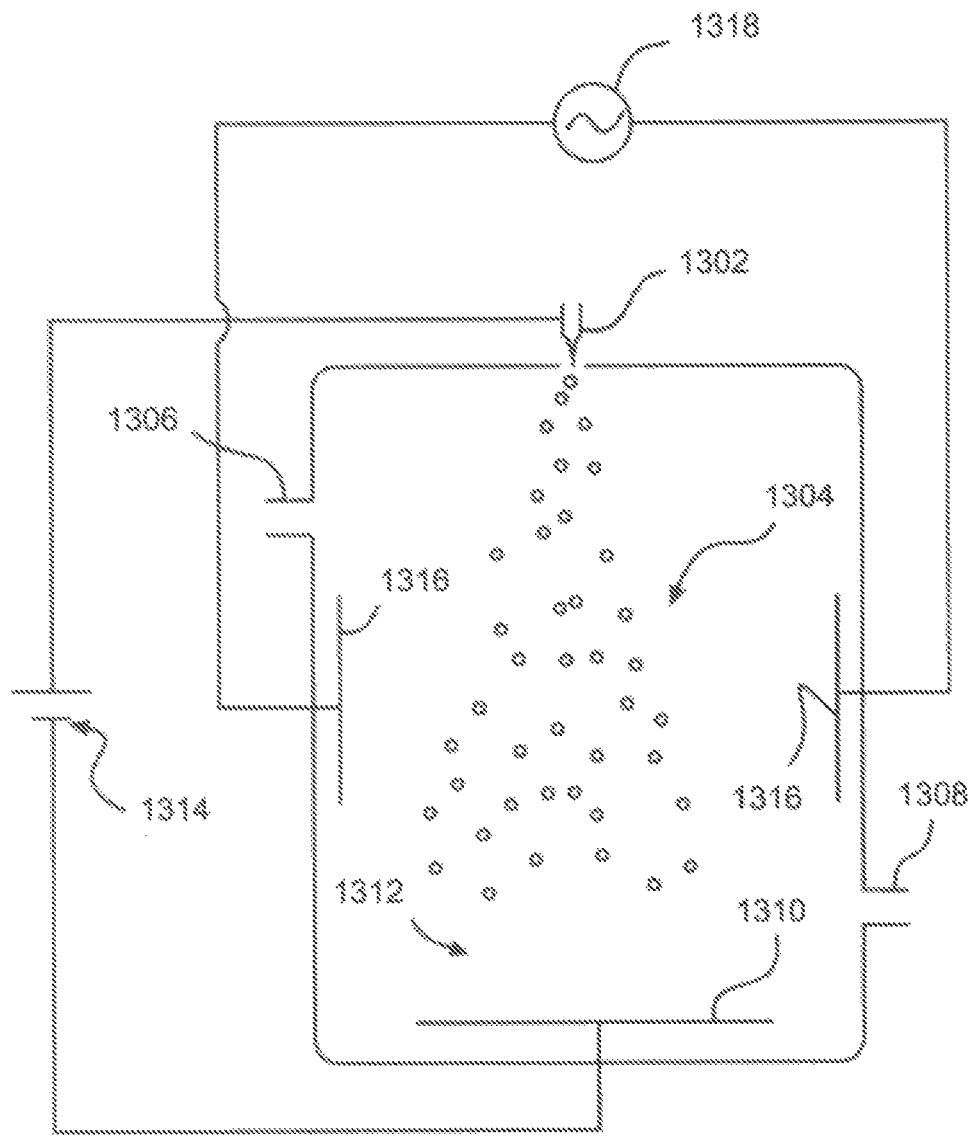
FIG. 13B is a schematic depicting a method of the invention based on a combination of chemical reactions between the electrospray and its surrounding gas phase, according to principles of the invention.

Referring to FIG. 13A, which illustrates an embodiment of the invention, a schematic of the electrospray methodology of the invention is provide. The electrospray methodology is based on a combination of chemical reactions between the electrospray and its surrounding gas phase. In FIG. 13A, the electrospray nozzle 1302 and cloud 1304 are depicted. Furthermore, the inlet 1306 and outlet port 1308, the counter-electrode 1310, the shell-forming reaction volume 1312, and the high-voltage DC source 1314 are also shown. The inlet 1206 may fill the shell-forming region or chamber with a gas containing the shell-forming monomer. the electrospray method of the invention offers the simplicity and scalability of single-liquid electrospray, thereby avoiding the use of multiple coaxial capillary nozzles altogether. Since electrosprays may be produce as low Reynolds numbers i.e., under conditions of low shear, the electrospray method of the invention produces true core-shell capsules without the low-yield and high-shear process penalties of emulsion-polymerization methods. Furthermore, the methodology also allows production of capsules much smaller than AC single-liquid electrospray.

In one embodiment, the electrospray may be delivered into a region in space whose gaseous environment has an adequate concentration of shell-forming monomer. As shown in FIG. 13A, the electrospray method may be made continuous or semi-continuous, depending on whether or not the supply of electrosprayed encapsulate containing liquid, the supply of monomer-containing gas, and the removal of encapsulated matter are all mad continuous. Since the shell-forming process is bound to stop after a certain shell thickness is achieved because the encased liquid core cannot deliver the components that react with the reactive monomers via diffusion toward the outer, growing shell indefinitely, the shell thickness of the vesicles may be controlled by controlling a number of process variables, such as but not limited to, monomer concentration, concentration of reactive species in the electrospray, temperature, time-of-flight of the electrospray, voltage, electrospray mean droplet size, and monomer and electrospray chemical properties, for example.

In another embodiment of the invention, the encapsulate-containing electrospray may be passed through a solution containing the shell-forming monomer, instead of a gas containing the said monomer.

In another embodiment, the electrospray method of the invention may be made discontinuous, and the time of suspension of the electrically charged spray within the cyanoacrylate containing gaseous volume may be extended by applying a high voltage AC potential within the said shell-forming reaction volume, as shown in FIG. 13B. Referring to FIG. 13B, the AC electrodes 1316, and the AC voltage source 1318 are shown. The fluid or solution containing the encapsulate may be first made into an electrospray cloud as depicted in FIG. 13A, but during some time point in the electrospray process, the DC high voltage and the fluid flow of encapsulate containing the fluid or solution switched off, while the AC voltage is turned on. Charged droplets may then be made to engage in oscillatory motion between the two AC electrodes 1316, and the frequency of the AC field is set so as to prevent the charge droplets striking one of the AC electrodes 1316. Turning off the AC high voltage source 1318 while turning the DC voltage back on after a desired amount of time has elapsed, permits collection of the vesicles in the DC counter-electrode 1310. By extending the time the electrospray remains suspended within the zone in which the shell of the vesicles is formed, the reaction may be controlled and the shell-forming time over a much larger range than with the setup shown in FIG. 13A may be achieved. A natural extension of the vesicle production scheme shown in FIG. 13B may be replace the gaseous environment in the shell forming chamber with an insulating fluid or solution bath containing the shell forming monomer or monomers.

In an alternative embodiment of the invention, a single fluid electrified jet may be employed, in the form of a solution or an emulsion to produce capsules having at least one entrapped agent. An emulsion, as used herein, generally refers to a single fluid that may be used to generate the particles instead of capsules with the EHD method as described above, using the same concentration ranges of the therapeutic components and other components, and the same average particle sizes as those of the capsules described below. Furthermore, magnetic nanoparticles may also be dispersed in the particles.

For example, an aqueous emulsified phase containing at least one agent, such as a therapeutic and/or imaging agent, and stabilizing salts and polyelectrolytes, may be dispersed in organic solutions containing at least one biopolymer. The resulting emulsion includes a biphasic medium which does not form distinct layers on electrified jet formation. The aqueous phase may be formulated in an identical manner as that of the core fluid in the case of the capsules described above, and the organic phase containing the biopolymer or biopolymers, which may also include magnetic nanoparticles and/or photonic particles formulated as that of the shell fluid of the capsules, as described above. Alternatively, a single fluid electrified jet formulation using certain co-solvents such as, but not limited to, dimethyl sulfoxide, leads to a homogeneous liquid mixture or solution comprising both the biopolymeric matrix precursor or precursors, and the active ingredients and receptors. The single electrified liquid jet approach may lead to entrapped, instead of encapsulated, active agents.

According to one embodiment, the shell-forming monomers may include compounds in the cyanoacrylate family, such as alkyl-substituted cyanoacrylates, for example. Moreover, the encapsulate-containing formulations may be compounds that readily react with the cyanoacrylate monomer to yield a skin of shell during the time-of-flight of the elctrospray toward the counter-electrode, without chemically altering the intended function of the encapsulate. In particular, the encapsulates may contain water. The encapsulates may be of biological origin, such as nucleic acids, DNA, DNA fragments thereof, RNA, RNA fragments thereof, proteins, lipids, carbohydrates, and combinations thereof and/or any modification thereof. Additionally, the encapsulates may include abiological therapeutic drugs, as described below.

According to one embodiment of the invention, the biopolymers that may be suitable for producing the shell of the EHD-derived capsules include, without limitation, PLA, PLGA, chitosan, alkyl metacrylates, and other bioabsorbable polymers such as PCL, starch, and co-polymers resulting from any combination thereof. Moreover, PEG may also be incorporated, either as polymer chains or as co-polymeric fragments to one or more of the other biopolymers, or functionalized with groups such as thio, carboxylic acid and amine groups. Additionally, other constituents may be incorporated in the shell fluid, such as nanosized magnetite particles having a size in the range of about 1 nm to about 300 nm and surfactants, prior to electrospray to yield a magnetically sensitive MRI material. Furthermore, nanosized photonic sensitive silver, gold, palladium or a combination thereof, having a size in the range of about 1 nm to about 50 nm may be added to the shell precursor fluid prior to electrospray to yield a photonic sensitive material.

According to another embodiment, core fluids suitable for the methodology of the invention may include aqueous phase with buffer salts and polyelectrolytes such as phosphate buffers to stabilize the solution structure of therapeutic agents of biological origin, one or more therapeutic agents such as, but not limited to, tumor necrosis factor alpha (TNF-$\alpha$) PROTEIN, TNF-$\alpha$, encoding cDNA for TNF-$\alpha$, OR Egr-TNF, one or more substances capable of inducing the action of Egr-TNF such as, but not limited to, Temozolomide, or TMZ, AND chemotherapy agents such as, but not limited to, acridinyl anisidide, allopurinol, altretamine, aminoglutethimide, androgen, arsenic trioxide, asparaginease, azacitidine, anti-angiogenesis, bleomycin, bortezomib, busulfan, capecitabine, carboplatin, carmustine, cetuximab, chlorambucil, cisplatin, cladribine, cyclophasphamide, dacarbazine, dactinomycin, daunorubicin, diethylstilbestro, docetaxel, doxorubicin, epirubicin, estramustine, etanidazole, etoposide, fluxuridine, fludarabine, 5-fluorouracil, flrosol DA, ftorafur, fulvestrant, gefitinib, gemcitabine, gemtuzumab ozogamicin, hydroxyurea, idarubicin, ifosfamide, interferon alpha, interleukin-2, irinotecan, levamisole, lomustine, mechloroethamine, melphalan, menogaril, methotrexate, methyl-CCNU, mitomcycin, mitoxantrone, oxaliplatin, paclitaxel, pemetrexed, pentostatin, picamycin, procarbazine, raltitrexed, steptozocin, ftorafur, temozolomide, teniposide, thalidomide, thioguanine, thiotepa, topotecan, tositumomab, trimetrexate, valspodar, vinblastine, vincristine, vindesine, vinorelbine, combinations thereof, and funtional equivalents thereof.

Moreover, the capsules or particles of the invention may contain chemotherapy-enhancing drugs, such as but not limited to, xcytrin, and chemotherapy protective drugs, such as but not limited to, amifostine. Certain radioactive elements may be suitable for the treatment and/or imaging of cancer, and in one embodiment of this invention, the radioactive elements can be incorporated in the electrospray generated particles. For example, Actinium-227 isotopic parent of Radium-223 is a so-called alpha emitter employed to treat metastases in the skeleton deriving from breast and prostate cancers, and for radioimmunotherapy, Copper-67 a gamma and beta emitter utilized in cancer radioimmunotherapy and lymphoma and colon and breast cancer diagnostics, Iodine-131, may be used for breast cancer treatment, leukemia, and lymphoma, using radioimmunotherapy, thyroid function and disease (e.g., cancer) studies, as well as non-malignant thyroid ailments (e.g., hyperthyroidism), Iodine-125, may be useful for implants for breast and prostate tumors, radiolabeling, prostate cancer brachytherapy, osteoporosis detection, tracer drugs, imaging diagnostics, mapping of brain receptors, brain cancer therapy, interstitial radiation treatment, determination plasma volume and glomerular filtration rate, deep vein thrombosis detection, Rhenium-186, useful for treatment and diagnosis of breast, colon, liver cancers and lymphoma via radioimmunotherapy, rheumatoid arthritis therapy, and bone cancer pain relief, and Yttrium-91, which is a gamma-emitting trace for Yttrium-90, which in turn is utilized for breast cancer radioimmunotherapy, and also lymphoma, kidney, colon, lung, prostate, ovarian, pancreatic, and liver cancers radioimmunotherapy.

In a further embodiment, radioactive isotopes may incorporated into the capsules of the invention, and their most frequent uses in medicine and related fields are: Cadmium-109 for general cancer detection, Actinium-225 and Thorium-229, the latter is the parent of Actinium-225 and grandparent of Bismuth-213 which are alpha emitters used in cancer radioimmunotherapy, Bismuth-212, and Thorium-228, the latter is the parent of Bismuth-212 which is an alpha emitter employed in cancer radioimmunotherapy, Cobalt-60, which is a radiation source for cancer radiotherapy, for food and medical supplies irradiation, Copper-64, a positron emitter employed for cancer therapy, Dysprosium-166, employed in cancer radioimmunotherapy, Erbium-169, useful for small-joint rheumatoid arthritis therapy, Europium-152 and Europium-154, useful as radiation sources for medical supplies and food irradiation, Gadolinium-153, useful for osteoporosis evaluation, Gold-198, useful for prostate and brain cancers, and for implants and intracavity treatment of ovarian cancer, Holmium-166, useful for myeloma therapy in targeted skeletal therapy, ablation of bone marrow, radiomunotherapy of cancer, and rheumatoid arthritis therapy, Iridium-192, useful for spinal cord and brain tumor treatment, brachytherapy, and treatment of blocked blood vessels, Lutetium-177, useful for treatment of blocked blood vessels and cancer radioimmunotherapy, Molybdenum-99, which is parent of Technetium-99m, which in turn is used for liver, brain, lungs, and heart imaging, and deep vein thrombosis detection, Osmium-194, useful for cancer radioimmunotherapy, Palladium-103, used in prostate cancer therapy, Platinum-195m, used in metabolism and biodistribution of cisplatin studies, Phosphorus-32, used for treatment of leukemia and polycythemia rubra vera (blood cell disease), bone cancer treatment and diagnosis, treatment of pancreatic, colon and liver cancer, treatment of blocked blood vessels and intracavity therapy, and diagnosis of surface tumors, Phosphorus-33, useful for leukemia therapy, treatment and diagnosis of bone disease, treatment of blocked blood vessels, and radiolabeling, Rhenium-188 useful for radioimmunotherapy, treatment of rheumatoid arthritis, bone cancer pain relief, and prostate cancer therapy, Rhodium-105, used for cancer radioimmunotherapy, Samarium-145, used for treatment of ocular cancer, Samarium-153, useful for cancer radioimmunotherapy and bone cancer pain relief, Scandium-47, useful for bone cancer pain relief and cancer radioimmunotherapy, Selenium-75, useful for detection of hyperactive parathyroid glands, as radiotracer in brain evaluations, adrenal cortex imaging via gamma scintigraphy, detection of steroid producing tumors, and pancreatic scans, Strontium-86, useful for brain scanning and bone cancer detection, Strontium-89 useful for treatment of multiple myeloma and bone cancer pain relief, Thulium-170, used as energy source for medical device implants, and as a gamma source in blood irradiators, Tin-117m, used in bone cancer pain relief and cancer immunotherapy, Tungsten-188, which is the parent of Rhenium-188, which in turn is used for cancer treatment and diagnosis, rheumatoid arthritis treatment, and treatment of blocked blood vessels and bone cancer pain relief, Xenon-127, used in pulmonary function evaluation, brain disorder imaging, and brain blood flow analysis, Ytterbium-175, used in cancer radioimmunotherapy, and Yttrium-90, which is obtained from Yttrium-89 and is useful for liver cancer treatment. Metallic or nonmetallic nanoparticles such as Ga and B which are used in neutron activation treatment can be co-encapsulated with therapeutic agents. The capsules or particles of this invention may optionally contain chemotherapy-enhancing drugs, such as but not limited to, xcytrin, and chemotherapy protective drugs, such as but not limited to, amifostine.

In another embodiment, the capsules of the invention may include at least one surface biochemical that may attach chemically or physically to enhance the affinity of the capsules for glioma cells, which may include epidermal growth factor, or EGF. The epidermal growth factor may either be incorporated onto the surface of the capsules post EHD processing, or during EHD processing as part of the shell fluid precursor. In particular, content range of EGF in the capsules and particles made by the methodologies of the invention may be in the range of about 0 to about 0.02 wt %. Moreover, other surface biochemicals and chemicals may include, intraleukin-13, intraleukin-4, peripheral type benzodiazephine, vascular endothelial growth factor, platelet-derived growth factor, fibroblast growoth factors, urokinase-type plasminogen activator, folic acid and folic acid derivatives, neurotrophin growth factor, somatostatin, cBSA, cHSA, protamine, insulin ApoE derived peptide, polysorbate-80, OX-26, transferring, glucose, mannose, RMP-7, thiamine, combinations thereof and functional equivalents thereof. The surface biochemicals may be of human, animal or recombinant origin and have a content in the range of about 0 to about 1 wt % for the non-estrogen based surface biochemicals.

In a further embodiment, the capsules may include at least one surface biochemical that may attach chemically or physically to enhance the affinity of the capsule for lymphoma, myeloma and leukemia such as VEGR-2, tositumomab, a monoclonal antibody which binds to the CD20 receptor, and other antibodies and monoclonal antibodies in particular those designed for other cluster of differentiation, such as but not limited to, CD5, CD7, CD13, CD19, CD22, CD33, CD52, and CD51, and antimyeloperoxidase any combinations thereof, and functional equivalents thereof. These biochemicals and their derivatives may either be incorporated onto the surface of the capsules post EHD processing, or during EHD processing as part of the shell fluid precursor. The content range of the surface receptors in the capsules is in the range of about 0.0 to about 1.0 wt %. Additional biochemicals and chemicals that may incorporate into the capsule may include, tyrosine kinase receptors, including fibroblast growth factor receptor (FGFR-1), EGF, TGF, VEGF-A, urokinase receptor, interleukin 4 receptor, retinoic acid receptor, heparin-binding EGF-like growth factor, or HB-EGF, amphiregulin, epiregulin, and neuregulins, human epidermal growth factor 2 (HER-2) and family members, erbB2 and erbB1 receptor family, intraleukin-13 and family derivatives, platelet-derived growth factor, urokinase-type plasminon activator, folic acid and folic acid derivatives, neurotrophin growth factor, somatostatin, combinations thereof, and functional equivalents thereof. The surface biochemicals may be of human, animal or recombinant origin, and may be present in a content range of about 0.0 to about 1.0 wt %.

In a yet further embodiment, the capsules may include at least one surface biochemical that may attach chemically or physically to enhance the affinity of the capsule for breast cancer is estrogen. Estrogen and its chemical derivatives may either be incorporated onto the surface of the capsules post EHD processing, or during EHD processing as part of the shell fluid precursor. The content range of estrogen or its derivates in the capsules and particles may be in the range of about 0.02 to about 0.4 wt %. Other surface biochemicals and chemicals that may be incorporated into the surface of the surface of the capsules and particles may include human epidermal growth factor 2 (HER-2) and family members, erbB2 and erbB1 receptor family, intraleukin-13 and family derivatives, vascular endothelial growth factor, platelet-derived growth factor, fibroblast growth factors, urokinase-type plasminon activator, folic acid and folic acid derivatives, neurotrophin growth factor, somatostatin, combinations thereof, and functional equivalents thereof. The surface biochemicals may be of human, animal or recombinant origin, and may be in a content range of about 0 to about 1 wt %.

In another embodiment, the capsules may include surface biochemical that may attach chemically or physically to enhance the affinity of the capsule for pancreatic cancer cells may be tyrosine kinase receptor, including fibrolast growth factor receptor (FGFR-1), EGF, TGF, VEGF-A, urokinase receptor, interleukin 4 receptor, retinoic acid receptor, heparin-binding EGF-line growth factor, or HB-EGF, amphiregulin, epiregulin, neuregulins, and functional equivalents thereof. These biochemicals and their derivative may either be incorporated onto the surface of the capsules post EHD processing, or during EHD processing as part of the shell fluid precursor. The content range of these surface receptors in the capsules or particles may be in the range of about 0.0 to about 1.0 wt %. Additional surface biochemicals and chemicals that may be incorporated into the surface of the capsules and particles may include human epidermal growth factor 2 (HER-2) and family members, erbB2 and erbB1 receptor family, intraleukin-13 and family derivatives, platelet-derived growth factor, urokinase-type plasminon activator, folic acid and folic acid derivatives, neurotrophin growth factor, somatostatin, combinations thereof, and functional equivalents thereof. The surface biochemicals may be of human, animal or recombinant origin, and may be in a content range of about 0 to about 1 wt %.

Moreover, other surface biochemicals and chemicals for the said capsules and particles may be fused in signal sequences, mitochondrial, nuclear, actin, and tubulin, golgi, plasma membrane, peroxisome, and may be in a content range of about 0.0 to about 1.0 wt %.

For example, according to one embodiment of the invention, the concentration of Paclitaxel in the capsules or particles may be in the range of about 10 to about 3200 µg/mL. Specifically, a concentration of TNA-α protein in the capsules or particles may be in the range of about 100 µg/mL to about 1,000 µg/mL. More specifically, a concentration of Egr-TNF in the capsules or particles may be in the range of about 10 µg/mL to about 300 µg/mL. The therapeutic effects may also be achieved with capsules containing either one or two compounds of the three-component, Paclitaxel, TNA-α and Egr-TNF group. Narrow ranges of the mass fractions of the therapeutic components and other capsules components, the capsules average size, average shell thickness, and narrow core to shell average mass ratios may be selected based on the location and size of the malignancy, and use magnetic nanoparticle doping to aid in the guiding of the said capsules to the malignancy may not be desired. For example, direct tumor injection, may be used in place of magnetically assisted delivery, and electromagnetic irradiation of the malignancy in contact with the particles or capsules by the methodologies of the invention may be used to trigger disruption of the particle with a concomitant release of therapeutic agents, to initiate biochemical processes such as, but not limited to, malignant cell DNA damage, or a combination of the said electromagnetic irradiation induced processes. DNA markers containing pCMV-Luc+plasmid containing the cytomegalovirum (CMV) promoter of pcDNA3 inserted upstream to the firefly luciferase of the pGL2-basic vector plasmid and TK renilla luciferase may also be used as markers.

In an alternate embodiment, convection enhanced delivery, or CED, may be used in place of magnetically assisted delivery, and electromagnetic irradiation of the malignancy in contact with the particles or capsules made by the methodologies of the invention may be used to trigger disruption of the capsule or particle with a concomitant release of therapeutic agents to initiate biochemical processes such as, but not limited to, malignant cell DNA damage, or a combination of the said electromagnetic irradiation induced processes.

The agents suitable for encapsulation or entrapment in the capsules of the invention should not be construed to be limited to agents suitable for cancer treatment or imaging of malignancy, as described above. However, alternative agents may be suitable for entrapment or encapsulation may include anti-inflammatory compounds, anti-allergics, glucocorticoids, anti-infective agents, antibiotics, antifungals, antivirals, mucolytics, antiseptics, vasoconstrictors, would healing agents, local anaesthetics, peptides, and proteins.

Examples of potentially useful anti-inflammatory compounds are glucocorticoids and non-steroidaol anti-inflammatory agents such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, elastane-, prostaglandin-, leukotriene, bradykin- antagonists, non-steroidal anti-inflammatory drugs (NSAIDs), such as ibuprofen, indometacin, including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of potentially useful antiallergic agents include the afore-mentioned glucocorticoids, and nedocromil, cetrizin, loratidin, montelukast, roflumilast, ziluton, omalizumab, heparins and heparinoids and other anntihistamins, Azelastine, Cetirizin, Desloratadin, Ebastin, Fexofenadin, Levocetirizin, Loratadin.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillins (mecillinam); cephalosporins, including cefazolins (cefazolin, cefazedone); cefuroximes (cerufoxim, cefamdole, cefotiam), cefoxitins (cefoxitin, cefotetan, latamoxef, flomoxef), cefotaximes (cefotaxime, ceftriaxone, ceftizoxime, cefmenoxime), ceftazidimes loracarbef, cefprozil), and cefixims (cefixime, cefpodoxim proxetile, cefuroxime axetil, cefetamet pivoxil, cefotiam hexetil), loracarbef, cefepim, clavulanic acid/amoxicillin, Ceftobiprole; synergists, including beta-lactamase inhibitors, such as clavulanic acid, sulbactam, and tazobactam; carbapenems, including imipenem, cilastin, meropenem, doripenem, tebipenem, ertapenem, ritipenam, and ibapenem; monobactams, including aztreonam; aminoglycosides, such as apramycin, gentamicin, amikacin, isepamicin, arbekacin, tobramycin, netilmicin, spectinomycin, streptomycin, capreomycin, neomycin, paromoycin, and kanamycin; macrolides, including drythromycin, clarythromycin, roxithromycin, azithromycin, dithromycin, josamycin, spiramycin and telithromycin; gyrase inhibitors or fluorquinolones, including ciprofloxacin, gatifloxacin, norfloxacin, ofloxacin, levofloxacin, perfloxacin, lomefloxacin, flerosacin, garenoxacin, clinafloxacin, sitafloxacin, prulifloxacin, olamufloxacin, caderofloxacin, gemifloxacin, balofloxacin, trovafloxacin, and moxifloxacin; tetracyclins, including tetracyclin, oxytetracyclin, rolitetracyclin, minocyclin, doxycycline, tigecycline and aminocycline; flycopeptides, including vancomycin, teicoplanin, ristocetin, avoparcin, oritavancin, ramoplanin, and peptide-4; polypeptides, including plectasin, dalbavancin, daptomycin, oritavancin, ramoplanin, dalbavancin, telavancin, bacitracin, tyrothricin, neomycin, kanamycin, mupirocin, paromomycin, plymyxin B and colistin; suflonamides, including sulfaidazine, sulfamethoxazole, sufalene, co-trimoxazole, co-trimozole, co-trimetrol, co-trimoxazine, and co-tetraxazine; azoles, including clotrimazole, oxiconazole, miconazole, ketoconazole, itraconazole, fluconazole, metronidazole, tinidazole, bifonazol, ravuconazol, posaconszol, voriconazoke, and ornidazole and other antofungs including flucytosin, griseofluvin, tonoftal, naftifin, terbinafin, amorolfin, ciclopiroxolamin, echnocandins, such as micafungin, caspofungin, anidulaafungin; nitrofurans, including introfurantoin and nitrofuranzone; -polyenes, including amphotericin B, natamycin, nystatin, flucocytosine; other antibiotics, including tithromycin, licomycin, clindamycin, oxazolindiones (linzezolids), ranbezolid, streptogramine A+B, pristinamycin aA+B, Virginiamycin A+B, dalfopristin/qiunupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocon B17, clerocidin, filgrastim, and pentamidine; antivirals, including aciclovir, ganciclovir, birivudin, valaciclovir, zidovudine, didanosin, thiacytidin, stavudin, lamivudin, zalcitabin, ribaviron, nevirapirin, delaviridin, trifluridin, ritonavir, saquinavir, indinavir, foscarnet, amantadin, podophyllotoxin, vidarabine, tromantadine, and proteinase inhibitors; plant extracts or ingredients, such as plant extracts from chamomile, hamamelis, echinacea, calendula, papain, pelargonium, essential oils, myrtol, pinen, limonen, cineole, thymol, mentol, tee tree oil, alpha-hederin, bisabolol, lycopodin, votapherole; would healing compounds including dexpantenol, allantoin, vitamins, hyaluronic acid, alpha-antitrypsin, anorganic and organic zine salts/compounds, interferones (alpha, beta, gamma), tumor necrosis factors, cytokines, interleukins.

Examples of potentially useful mucolytics are DNase, P2Y2-agonists (denufosol), heparinoids, guaifenesin, acetylcysteine, carbocysteine, ambroxol, bromhexine, lecithins, myrtol, and recombinant surfactant proteins.

Examples of potentially useful local anaesthetic agents include benzocaine, tetracaine, procaine, lidocaine and bupivacaine.

Examples of potentially useful antiallergic agents include the afore-mentioned glucocorticoids, nedocromil. Examples of potentially useful peptides and proteins include antibodies against toxins produced by microorganisms, antimicrobial peptides such as cecropins, defensins, thionins, and cathelicidns.

Also, immunmodulators including methotrexate, azathioprine, cyclosporine A, tacrolimus, sirolimus, rapamycin, mycofenolate, mofetil, cytotatics and metastasis inhibitors, alkylants, such as nimustine, melphanlane, carmustine, lomustine, cyclophosphosphamide, ifosfamide, trofosfamide, chlorambucil, busulfane, treosulfane, prednimustine, thiotepa; antimetabilites, e.g. cytarabine, fluorouracil, methotrexate, mercaptopurine, tioguanine; alkaloids, such as vinlbastine, vincristine, vindesine; antibiotics, such as alcarubicine, bleomyicne, dactinomycine, daunorubicine, doxorubicine, epirubicine, idarubicine, mitomycine, plicamycine; complexes of secondary group elements (e.g. Ti, Zr, V, Nb, Ta, Mo, W, Pt) such as carboplatinu, cis-platinum and tallocene compounds such as titanocendichloride; amsacrine, dacarbazine, estramustine, etoposide, beraprost, hydroxycarbamide, mitoxanthrone, procaazine, temiposide; paclitaxel, iressa, zactima, poly-ADP-ribose-polymerase (PRAP) enzyme inhibotors, banoxantrone, gemcitabine, pemetrexed, bevacizumab, ranibizumab may be suitable for entrapment or encapsulation in the capsules of the invention.

In a further embodiment other compounds may include proteinase inhibitors, such as a-anti-trypsin; antioxidants, such as tocopherols, glutathion; pituitary hormones, hypothalamic hormones, regulatory peptides and their inhibiting agents, corticotropine, tetracosactide, choriogonandotropine, urofolitropine, urogonadotropine, saomatotropine metergoline, desmopressine, oxytocine, argipressine, ornipressine, leuproreline, triptoreline, gonadoreline, busereline, nafareline, goselerine, somatostatine; parathyroide gland hormones, clacium metabolism regulators, dihydrtachysterole, calcitonine, clodronic acid, etidronic acid; thyroid gland therapeutics; sex hormones and their inhibiting agents, anabolics, androgens, estrogens, gestagenes, antiestrogenes; anti-migraine drugs, such as proxibabal, lisuride, methysergide, dihydroergotamine, ergotamine, clonidine, pizotifene; hypnotics, sedatives, benzodiazepines, barbiturates, cyclopyrrolines, imdazopyridines, antiepileptics, zolpidem, barbiturates, phenytoin, primidone, mesuximide, ethosuximide, sultiam, carbamazepin, valproic acid, vigabatrine, antiparkinson drugs, such as levodopa, carbidopa, benserazie, selegiline, bromocriptine, amantadine, tiapride; antiemetics, such as thiethylperacine, bromopride, domperidone, gransietrone, ondasetrone, tropisetrone, pyridoxine; analgesics, such as buprenorphone, fentanyl, morphine, codeine, hydromorphone, methadone, fenpipramide, fentanyl, piritramide, pentazocine, buprenorphine, nalbuphine, tilidine; drugs for narcosis, such as N-methylated barbiturates, thiobarbiturates, ketamine, etomidate, propofol, benzodiazepines, droperidol, haloperidol, alfentanyl, sulfentanyl; antirheumatism drugs including tumor necrosis factor-alfa, nonsteroidal antiinflammatory drugs; antidiabetic drugs, such as insulin, sulfonylurea derivatives, biguanids, glitizols, glucagon, diazoxid; cytokines, such as interleukines, interferones, tumor necrosis factor (TNF), colony stimulating factors (GM-CSF, G-CSF, M-CSF); proteins, e.g. epoetine, and peptides, e.g. parathyrin, somatomedin C; heparine, heparinoids, urokinases, streptokinases, ATP-ase, prostacycline, sexual stimulants, or genetic material.

The description and examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the material sciences, polymer sciences, or related fields are intended to be within the scope of the appended claims.

The disclosures of all references and publications cited above are expressly incorporated by reference in their entireties to the same extend as if each were incorporated by reference individually.

EXAMPLES

Specific Example 1

This example describes an encapsulation of a protein solution using a modification of the shell formulation that consisted of a solution of bovine serum albumin (BSA) in the presence of salts such as phosphates to stabilize the pH of the solution. Confocal fluorescence microscopy (CFM) and BSA with a fluorescent tag was used for visualizing the capsule. About 2 mg fluorescent protein was dissolved in about 1 mL of phosphate-buffer saline (PBS), type buffer that stabilized the acid-base properties of this aqueous solution to a pH equal to about 7.4.

The final BSA concentration was adjusted to about 3 µM. Silica sol was used as the shell fluid precursor following the sol aging procedures, with addition of tert-amyl alcohol to a 50:50 volume ratio.

In general, for solution aging purposes, an acidified tetraethyl orthosilicate solution in ethanol may be aged at about 80° C. for about 4 to about 6 hours. Tert-amyl alcohol was added to increase the hydrophbicity of the shell fluid, which further prevented any significant mixing between core and shell fluids.

Figure 14:
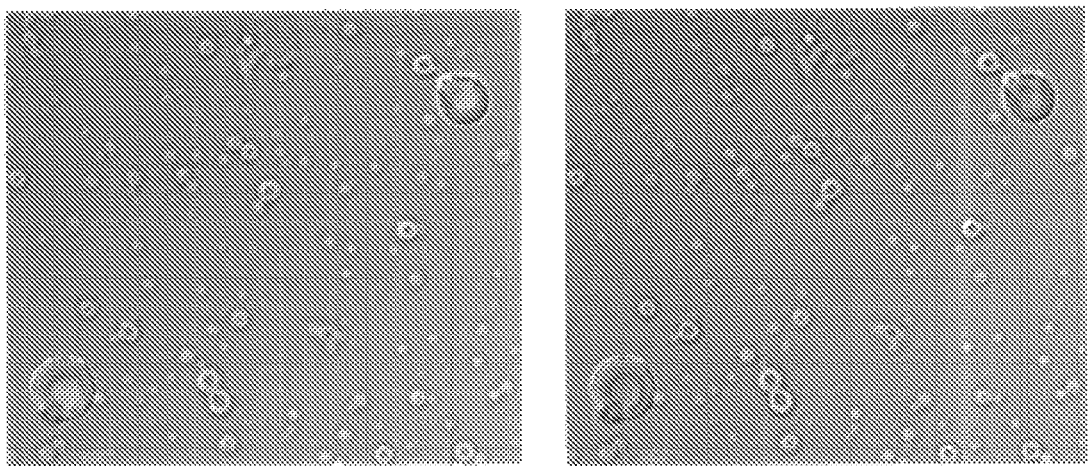
FIG. 14 shows a photograph obtained by confocal microscopy. Panel I is the unfocused signal and Panel II shows a focuses signal in the core fluid region of the capsule.

The core and shell flow rates were adjusted to about 0.025 and about 0.75 mL/h, respectively, Adequate voltages for capsule design were in the range of about 11 to about 12 kV, and the distance between the two-fluid electrified meniscus and the collection zone was in the range of about 4 to about 14 cm. The collection zone, or collector electrode, was a flat metal surface kept at ground electrical potential, whereas the two-fluid electrified meniscus were kept at a positive electrical bias in the range of about 5 to about 18 kV. FIG. 14 shows photographs obtained with the aid of the CFM technique, in which confinement of BSA was evident when the instrument was focused to yield a fluorescent signal in the core fluid region of the capsules. Referring to FIG. 14, Panel I shows the unfocused fluorescent signal and Panel II shows the focused fluorescent signal.

Specific Example 2

The sol-gel methods and process variables used to encapsulate fluorescent BSA in Specific Example 1 were slightly modified to encapsulate a transaminase. This enzyme was used to catalyze the following reaction:

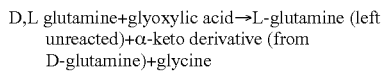

D,L glutamine+glyoxylic acid→L-glutamine (left unreacted)+α-keto derivative (from D-glutamine)+glycine Each enantiomeric form has the ability to rotate polarized light, and a technique known as polarimetry may be used to follow chemical reactions involving enantiomers as a function of time. The reactants, on the left side of the reaction shown above, are basically a mixture with no optical activity, since the D,L prefix stands for about a 50:50 mixture of the D and L enantiomers of glutamine. The products, on the right hand side of the reaction shown above, become enriched in unreacted L-glutamine with a concomitant time-dependent optical rotation signal that may be tracked by polarimetry, because this particular transaminase only catalyzes reactions involving D enantiomers. The reaction was buffered to a about pH of 7.5 with PBS.

Since the specific rotation of the glutamine isomers was low in pure water, an experimental scheme was devised to both stop the reaction prior to polarimetry quantification at different reaction times, and to increase the sensitivity of the analytical technique. This was achieved by addition of about 1.0 mL of 5 M HCl to an aliquot taken from the reactor, which denatures the enzyme. The enzyme catalyst either settles at the bottom of the vial, or was removed by centrifugation, and acidification increased the sensitivity of the polarimetry technique by about ½ order of magnitude relative to the observed in nearly neutral solutions.

Figure 15:
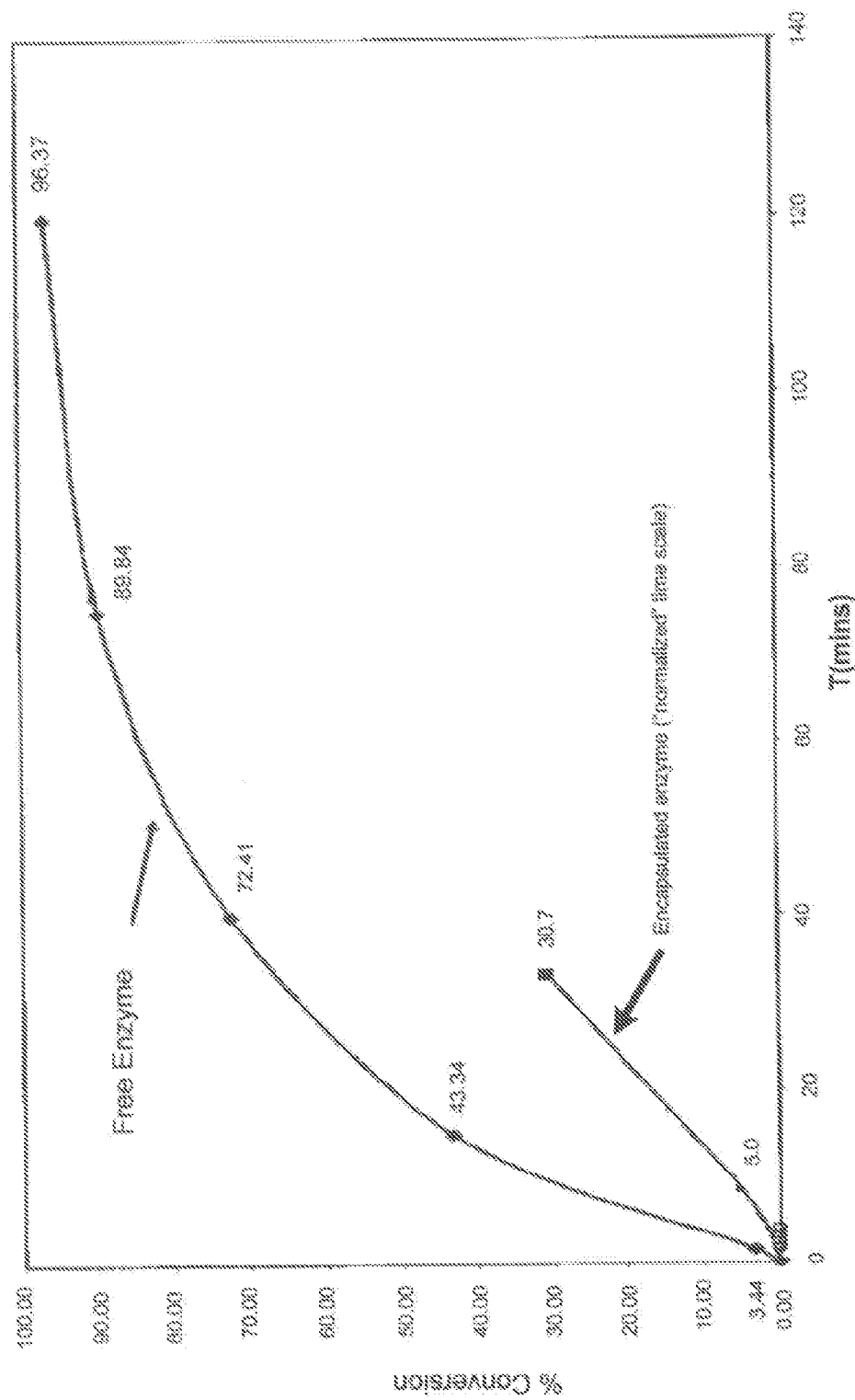
FIG. 15 is a graph showing the activity of transaminase in both its encapsulated and in free solution, once rotation is converted to an equivalent D- (or L-) glutamine concentration via calibration curves.

The biocatalytic test was run using about 50 mM concentrations of the substrates, and enzyme concentrations of about 0.5 mg/mL. FIG. 15 shows an example of the activity of this transaminase in both its encapsulated state, and free in solution, once optical rotation was converted to an equivalent D- (or L-) glutamine concentration via previous determination of calibration curves.

Specific Example 3

Particles with 3.1 LACZ as DNA Marker

The therapeutic solution was prepared by mixing 3.1 LACZ in about 10 mM Bis-Tris propane buffer aqueous solution containing about 1 wt % of isopropanol and about 2 mM of $CaCl_2$. The final concentration of 3.1 LACZ was 700 µg/mL.

A biopolymer solution was prepared by mixing two functionalized biopolymers in chloroform: (a) COOH-poly(ethylene glycol)-b-polylactide, or PEG-b-PLA, with a molecular weight of 200-b-1940 Da using same nomenclature, respectively, and a Mw/Mn=1.2; and (b) Poly(caprolactone)-SH, or PCSH, with a molecular weight of 5,000 Da and a Mw/Mn=1.5. This solution was doped with a solution of magnetite particles with an average diameter of about 15 nm. The weight percent contents of PEG-b-PLA, PCSH, and magnetite particles in this solution were about 0.071 wt %, about 0.058 wt %, and about 0.004 wt % respectively.

The therapeutic and biopolymer solutions were mixed and dimethyl sulfoxide, or DMSO, was added to form a homogenous solution. particles with an average diameter in the range of about 0.250 to about 1 μm were made produced, but smaller capsules may be made by varying the process variables. Specifically, the flow rate used was about 0.150 mL/h, and the external voltage was about 7 kV.

Specific Example 4

Encapsulation of PDs Red 2 NUC

The compound in this example was formed by the two-jet system depicted in FIG. 5. The core fluid solution was first prepared by mixing PDs red 2 NUC and about 10 mM Bis-Tris propane aqueous solution containing about 1 wt % of isopropanol and about 2 mM of $CaCl_2$. The final concentration of PDs red 2 NUC in the core fluid solution was about 22.5 μg/mL.

The shell fluid solution was prepared by mixing two functionalized biopolymers in chloroform: (a) COOH-poly(ethylene glycol)-b-polylactide, or PEG-b-PLA, with a molecular wiight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH in the shell fluid solution were about 0.29 wt % and about 0.31 wt %, respectively.

Capsules with an average diameter in the range of about 0.250 μm to about 1 μm were produced. Specifically, the core and shell fluid flow rates used were about 0.050 and about 0.300 mL/h, respectively, and the external voltage was about 7 kV.

Capsules with a PDs red 2 NUC loading in the range of about 0.01 to about 25% by weight of the added polymer may be made by this method by adjusting the concentration of the core fluid solution.

Specific Example 5

Encapsulation of Green Fluorescent Protein

The core fluid solution was prepared by mixing Green Fluorescent Protein, or GFP, and about 10 mM Bis-Tris propane aqueous solution containing about 1 wt % of isopropanol and about 2 mM of $CaCl_2$. The final concentration of GFP in the core fluid solution was about 30 μg/mL.

The shell fluid solution was prepared by mixing two functionalized biopolymers in chloroform: (a) COOH-poly(ethylene glycol)-b-polyactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH were about 0.32 wt % and about 0.31 wt %, respectively.

Capsules with an average diameter in the range of about 0.250 μm to about 1 μm were made produced, but smaller capsules may be made by adjusting the process variables. Specifically, the core and shell fluid flow rates used were about 0.050 and about 0.300 ml/h, respectively, and the external voltage was about 8 kV.

Capsules with a GFP loading in the range of about 0.01 to about 20% by weight of the added polymer were made by this method by adjusting the concentration of the core fluid solution.

Specific Example 6

Particles with Doxorubicin with Folic Acid Functional Groups

The therapeutic solution is prepared by dissolving Doxorubicin hydrochloride, or DOXO, in dichloromethane. The concentration of DOXO in the therapeutic solution is about 1,000 μg/mL.

A biopolymer solution is prepared by mixing two functionalized biopolymers in chloroform: (a) Folate-functionalized poly(ethylene glycol), or Folate-PEG, with a molecular weight of 5,000 Da and (b) Poly(caprolactone)-SH, or PCSH, with a molecular weight of 5,000 Da and a Mw/Mn=1.5. The weight percent contents of Folate-PEG and PCSH are about 0.30 wt % and about 0.30 wt %, respectively.

The therapeutic and biopolymer solutions are mixed to form a homogenous solution. Particles with an average diameter in the range of about 0.250 μm to about 1 μm are produced, but smaller capsules may be made by adjusting the process variables. Specifically, the flowrates used are in the range of about 0.050 to about 0.300 ml/h. The external voltage is about 7.5 kV.

Particles with a DOXO loading in the range of about 0.01 to about 25% by weight of the added polymer may be made by this method by adjusting the concentration of the core fluid solution.

Specific Example 7

Encapsulation of Doxorubicin

The core fluid solution were prepared by mixing doxorubicin hydrochloride, or DOXO in about 10 mM Bis-Tris propane aqueous solution containing about 1 wt % of isopropanol and about 2 mM of $CaCl_2$. The final concentration of DOXO in the core fluid solution was about 1,000 μg/mL.

The shell fluid solution was prepared by mixing two functionalized biopolymers in chloroform: (a) COOH-poly (ethylene glycol)-b-polyactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight about 0.3 wt % and about 0.3 wt %, respectively.

Capsules with an average diameter in the range of about 0.250 μm to about 1 μm were produced, but smaller capsules may be made by adjusting the process variables. Specifically, the core and shell fluid flow rates used were 0.050 and 0.300 ml/h, respectively, and the external voltage was 8.5 kV.

Capsules with a DOXO loading in the range of about 0.01 to about 23% by weight of the added polymer may be made by this method by adjusting the concentration of the core fluid solution.

Specific Example 8

Encapsulation of Cobalt Nanoparticles

The core fluid solution was prepared by mixing an aqueous solution of cobalt nanoparticles, or NP-Co and a 10 mM Bis-Tris propane aqueous solution containing about 1 wt % of isopropanol and about 2 mM of $CaCl_2$. The final concentration of NP-Co in the core fluid solution was in the range of about 1,000 to about 500 μg/mL.

The shell fluid solution was prepared by mixing two functionalized biopolymers in chloroform: (a)COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH were about 0.30 wt % to about 0.30 wt %, respectively.

Capsules with an average diameter in the range of about 0.250 μm to about 1 μm were produced, but smaller capsules may be made by adjusting the process variables. Specifically, the core and shell fluid flow rates used were in the range of about 0.050 to about 0.150 ml/h, respectively, and the external voltage was about 8 kV.

Capsules with a nonoparticle (Np)-Co loading in the range of about 0.01 to about 11% by weight of the added polymer may be made by this method by adjusting the concentration of the core fluid solution.

Specific Example 9

Particles with Doxorubicin with EGF Functional Groups

The therapeutic solution is prepared by dissolving Doxorubicin hydrochloride, or DOXO, in dichloromethane. The concentration of DOXO in the therapeutic solution is about 1,000 μg/mL.

A biopolymer solution is prepared by mixing two functionalized biopolymers in chloroform: (a) EGF-functionalized poly)ethylene glycol), or EGF-PEG, with a molecular weight of 5,000 Da, and (b) Poly(caprolacton)-SH, or PCSH, with a molecular weight of 5,000 Da and a Mw/Mn=1.5. The weight percent contents of EGF-PEG and PCSH are about 0.30 wt % and about 0.30 wt %, respectively.

The therapeutic and biopolymer solutions are mixed to form a homogenous solution. Particles with an average diameter in the range of about 0.250 μm are produced, but smaller capsules may be made by adjusting the process variables. Specifically, the flowrates used are in the range of about 0.50 to about 0.300 ml/h range. The external voltage is about 7.5 kV.

Particles with a DOXO loading in the range of about 0.01 to about 25% by weight of the added polymer may be made by adjusting the concentration of the core fluid solution.

Specific Example 10

Particles with Luciferase as DNA Marker

The therapeutic solution is prepared by mixing Luciferase in a 10 mM Bis-Tris propane buffer aqueous solution containing about 1 wt % of isopropanol and about 2 mM of CaCl$_2$. The final concentration of Luciferase is about 334.5 μg/mL.

A biopolymer solution is prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and (b) Poly(caprolactone)-SH, or PCSH, with a molecular weight of 5,000 Da and a Mw/Mn=1.5. This solution is doped with a solution of magnetite particles with an average diameter of about 15 nm. The weight percent contents of PEG-b-PLA, PCSH, and magnetite particles in this solution are about 0.071 wt %, about 0.058 wt %, and about 0.004 wt % respectively.

The therapeutic and biopolymer solutions are mixed and dimethyl sulfoxide, or DMSO, is added to form a homogenous solution. Particles with an average diameter in the range of about 0.250 to about 1 μm are produced, but smaller capsules may be made by varying the process variables. Specifically, the flow rate used was about 0.150 mL/h, and the external voltage was about 7 kV.

Particles with a Luciferase loading in the range of about 0.01 to about 63% by weight of the added polymer may be made by adjusting the concentration of the Luciferase-containing solution.

Specific Example 11

Particles with TK Renilla Luciferase as DNA Marker

The therapeutic solution was prepared by mixing TK Renilla Luciferase in about 10 mM Bis-Tis propane buffer aqueous solution containing about 1 wt % of isopropanol and about 2 mM of CaCl$_2$. The final concentration of TK Renilla Luciferase was about 334.5 μg/mL.

A biopolymer solution was prepared by mixing two functionalized biopolymes in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. This solution was doped with a solution of magnetite particles with an average diameter of about 15 nm. The weight percent contents of PEG-b-PLA, PCSH, and magnetite particles in this solution were about 0.071 wt %, and about 0.058 wt %, and about 0.004 wt % respectively.

The therapeutic and biopolymer solutions were mixed and DMSO was added to form a homogenous solution. particles with an average diameter in the range of about 0.250 to about 1 μm were produces, but smaller capsules may be made by varying the process variable. Specifically, the flow rate used was about 0.150 mL/h, and the external voltage was about 7 kV.

Particles with a TK Renilla Luciferase loading in the range of about 0.01 to about 63% by weight of the added polymer may be made by adjusting the concentration of the TK Renilla Luciferase-containing solution Specific Example 12

Encapsulation of Cobalt Nanoparticles in Capsules Containing EGF and Mitochandria Localization Vector The core fluid solution is prepared by mixing an aqueous solution of cobalt nanoparticles, or NP-Co and 10 mM Bis-Tris propane aqueous solution containing about 1.0 wt % of isopropanol and about 2 mM of CaCl$_2$. The final concentration of NP-Co in the core fluid solution is in the range of about 1,000 to about 500 μg/ml.

The shell fluid solution is prepared by mixing three functionalized biopolymers in chloform: (a) COOH-poly(ethylene glycol)-b-polylactide, or PEG-b-PLA, with a molecular weight of 2000-b-1940 Da using same nomenclature, respectively, and a Mw/Mn=1.2; (b) Poly(caprolactone)-SH, or PCSH, with a molecular weight of 5,000 Da and Mw/Mn=1.5; and (c) EGF-functionalized poly(ethylene glycol), or EGF-PEG, with a molecular weight of 5,000 Da. The weight percent contents of PEG-b-PLA, PCSH and EGF-PEG are about 0.30 wt %, about 0.30 wt % and about 0.10 wt %, respectively.

A buffer solution containing a plasmid subcellular localization vector targeted to the mitochondria is added. The concentration of the vector in the shell fluid solution is in the range of about 0.0 to about 1.0 wt %. DMSO is added to form a homogenous solution.

Capsules with an average diameter in the range of about 0.250 µm to about 1 µm are produced, but smaller capsules may be made by adjusting the process variables. Specifically, the core and shell fluid flow rates used were about 0.050 and about 0.150 ml/h, respectively, and the external voltage was about 8 kV.

Capsules with a Np—Co loading in the range of about 0.01 to about 11% by weight of the added polymer may be made by adjusting the concentration of the core fluid solution.

Specific Example 13

Encapsulation of Chlorambucil in Capsules Containing CD19 Functional Groups on the Shell The core fluid solution was prepared by dissolving Chlorambucil in about 10 mM Bis-Tis propane aqueous solution containing about 1 wt % of isopropanol, about 2 mM of $CaCl_2$ and DMSO. The final concentration of Chlorambucil in the core fluid solution was in the range of about 2,000 to about 500 µg/mL.

The shell fluid solution was prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH were about 0.05 wt % and about 0.05 wt %, respectively. The shell fluid solution was mixed with a solution containing CD19 dissolved in a mixture of dichloromethane and polyethylene oxide (MW=400-1000).

Capsules with an average diameter in the range of about 0.250 µm to about 1 µm were produced, but smaller capsules may be made by adjusting the process variables. Specifically, the core and shell fluid flow rates used were about 0.050 and about 0.150 ml/h, respectively, and the external voltage was about 8 kV.

Capsules with a Chlorambucil loading in the range of about 0.01 to about 20.0% by weight of the added polymer may be made by adjusting the concentration of the core fluid solution. Capsules with a CD19 loading in the range of about 5 to about 100 µg per mg of the added polymer may be produced by adjusting the concentration of the shell fluid solution.

Specific Example 14

Encapsulation of Chlorambucil in Capsules Containing CD20 Functional Groups

The core fluid solution was prepared by dissolving Chlorambucil in a about 10 mM Bis-Tris propane aqueous solution containing about 1.0 wt % of isopropanol, about 2.0 mM of $CaCl_2$ and DMSO. The final concentration of Chlorambucil in the core fluid solution was in the range of about 2,000 to about 500 µg/mL.

The shell fluid solution was prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH were about 0.05 wt % and about 0.05 wt %, respectively. The shell fluid solution was mixed with a solution containing CD20 dissolved in a mixture of dichloromethane and polyethylene oxide (MW=400-1000).

Capsules with an average diameter in the range of about 0.250 µm to about 1 µm were generated, but smaller capsules may be made by adjusting the process variables. Specifically, the core and shell fluid flow rates used were about 0.050 and about 0.150 ml/h, respectively, and the external voltage was about 8 kV.

Capsules with a Chlorambucil loading in the range of about 0.01 to about 20.0% by weight of the added polymer may be made by adjusting the concentration of the core fluid solution. Capsules with a CD20 loading in the range of about 5 to about 100 µg per mg of the added polymer may be made by adjusting the concentration of the shell fluid solution.

Specific Example 15

Encapsulation of Chlorambucil and Hydrochloroquine Sulfate in Capsules Containing CD19 and CD20 Functional Groups The core fluid solution was prepared by dissolving Chlorambucil and Hydrochloroquine sulfate, or HCQ, in about 10 mM Bis-Tris propane aqueous solution containing about 1.0 wt % of isopropanol, 2 mM of $CaCl_2$ and DMSO. The final concentrations of Chlorambucil and HCQ in the core fluid solution were in the range of about 2,000 to about 500 µg/mL.

The shell fluid solution was prepared by mixing two functinalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH are 0.05 wt % and 0.05 wt %, respectively. The shell fluid solution was mixed with a solution containing CD19 and CD20 dissolved in a mixture of dichloromethane and polyethylene oxide (MW=400-1000).

Capsules with an average diameter in the range of about 0.250 µm to about 1 µm were produced, but smaller capsules may be made by adjusting the process variables. Specifically, the core and shell fluid flow rates used were about 0.050 and about 0.300 ml/h, respectively, and the external voltage was about 8 kV.

Capsules with a Chlorambucil and HCQ loading in the range of about 0.01 to about 20.0% each by weight of the added polymer may be made by adjusting the concentration of the core fluid solution. Capsules with a CD19 AND CD20 loading in the range of about 5 to about 100 µg each per mg of the added polymer may by adjusting the concentration of the shell fluid solution.

Specific Example 16

Encapsulation of Chlorambucil in Capsules Containing CD19 Functional Group and Golgi Complex Localization Vector The core fluid solution is prepared by dissolving Chlorambucil in about 10 mM Bis-Tris propane aqueous solution containing about 1 wt % of isopropanol, about 2 mM of $CaCl_2$ and DMSO. The final concentration of Chlorambucil in the core fluid solution is in the range of about 2,000 to about 500 µg/mL.

The shell fluid solution was prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH are 0.05 wt % and 0.05 wt %, respectively. The shell fluid solution was mixed with a solution containing CD19 dissolved in a mixture of dichloromethane and polyethylene oxide (MW=400-1000).

A buffer solution containing a plasmid subcellular localization vector targeted to the Golgi complex is added. The concentration of the vector in the shell fluid solution is in the range of 0 to 1 wt %. DMSO is added to form a homogenous solution.

Capsules with an average diameter in the range of about 0.250 µm to about 1 µm are produced, but smaller capsules may be made by adjusting the process variable. Specifically, the core and shell fluid flow rates used are about 0.50 and about 0.150 ml/h, respectively, and the external voltage is about 8 kV.

Capsules with a Chlorambucil loading in the range of about 0.01 to about 20.0% by weight of the added polymer may be produced by adjusting the concentration of the core fluid solution. Capsules with a CD19 loading in the range of about 5 to about 100 µg per mg of the added polymer may be made by adjusting the concentration of the shell fluid solution.

Specific Example 17

Particles Containing Iodine-125 and EGF Functional Groups

The therapeutic solution is prepared by dissolving Iodine-125 in dichloromethane. The concentration of Iodine-125 in the therapeutic solution is about 1,000 µg/mL.

The biopolymer solution is prepared by mixing two functionalized biopolymers in chloroform: (a) EGF-functionalized poly(ethylene glycol),or EGF-PEG, with a molecular weight of 5,000 Da, and (b) Poly(caprolactone)-SH, or PCSH, with a molecular weight of 5,000 Da and a Mw/Mn=1.5. The weight percent contents of EGF-PEG and PCSH are about 0.30 wt % and 0.030 wt %, respectively.

The therapeutic and biopolymer solutions are mixed to form a homogenous solution. Particles with an average diameter in the range of about 0.20 µm to about 1 µm are produced, but smaller capsules may be made by adjusting the process variables. Specifically, the flowrates used are in the range of 0.050 to about 0.300 ml/h. the external voltage is about 7.5 kV.

Particles with an Iodine-125 loading in the range of about 0.01 and 25% by weight of the added polymer may adjusting the concentration of the core fluid solution.

Specific Example 18

Encapsulation of Chlorambucil in Capsules Containing Ga/Fe Nanoparticles and Epidermal Growth Factor Receptor The core fluid solution is prepared by dissolving Chlorambucil in a 10 mM Bis-Tris propane aqueous solution containing about 1.0 wt % of isopropanol, about 2.0 mM of $CaCl_2$ and DMSO. The final concentration of Chlorambucil in the core fluid solution is in the range of about 2,000 to about 500 µg/mL.

The shell fluid solution is prepared by mixing two functionalized biopolymers in chloroform: (a) Epidermal growth factor-functionalized poly(ethylene glycol), or EGF-PEG, with a molecular weight of 5,000 Da, and (b) Poly(caprolactone)-SH, or PCSH, with a molecular weight of 5,000 Da and a Mw/Mn=1.5. This solution is doped with a solution of $Fe_3O_4$ and $Ga_2O_3$ nanoparticles with an average diameter of about 15 nm. The weight percent contents of EGF-PEG, PCSH, $Fe_3O_4$ and $Ga_2O_3$ in the shell fluid solution are about 0.071 wt %, about 0.058 wt %, about 0.004 wt % and about 0.004 wt %, respectively.

Particles with an average diameter in the range of about 0.250 µm to about 1 µm are produced, but smaller capsules may be made by adjusting the process variables. Specifically, the flowrates used are in the range of about 0.050 to about 0.300 ml/h. The external voltage is about 7.5 kV.

Particles with a Chlorambucil loading in the range of about 0.01 to about 25.0% by weight of the added polymer may be made by adjusting the concentration of the core fluid solution.

Specific Example 19

Encapsulation of Chlorambucil in Capsules Containing Ga/B/Fe Nanoparticles and Epidermal Growth Factor Receptor The core fluid solution is prepared by dissolving Chlorambucil in about 10.0 mM Bis-Tris propane aqueous solution containing about 1.0 wt % of isopropanol, about 2.0 mM of $CaCl_2$ and DMSO. The final concentration of Chlorambucil in the core fluid solution is in the range of about 2,000 to about 500 µg/mL.

The shell fluid solution is prepared by mixing two functionalized biopolymers in chloroform: (a)Epidermal growth factor-functionalized poly(ethylene glycol), or EGF-PEG, with a molecular weight of 5,000 Da and (b) Poly(caprolactone)-SH, or PCSH, with a molecular weight of 5,000 Da and a Mw/Mn=1.5. The solution is doped with a solution of $Fe_3O_4$, $Ga_2O_3$ and $B_2O_3$ nanoparticles with an average diameter of about 15 nm. The weight percent contents of EGF-PEG, PCSH $Fe_3O_4$, $Ga_2O_3$ and $B_2O_3$ in the shell fluid solution are about 0.071 wt %, about 0.058 wt %, about 0.004 wt %, about 0.004 wt % and about 0.004 wt %, respectively.

Particles with an average diameter in the range of about 0.250 µm to about 1 µm are produced, but smaller capsules may be made by adjusting the process variables. Specifically, the flowrates used are in the range of about 0.050 to about 0.300 ml/h. The external voltage is about 7.5 kV.

Particles with a Chlorambucil loading in the range of about 0.01 to about 25% by weight of the added polymer may be made by adjusting the concentration of the core fluid solution.

Specific Example 20

Particles and Paclitaxel with Folic Acid Functional Groups

The therapeutic solution is prepared by dissolving paclitaxel in dichloromethane. The concentration of Paclitaxel in the therapeutic solution is about 1,000 µg/mL.

A biopolymer solution is prepared by mixing two functionalized biopolymers in chloroform: (a) Folate-functionalized poly(ethylene glycol), or Folate-PEG, with a molecular weight of 5,000 Da, and (b) Poly(caprolactone)-SH, or PCSH, with a molecular weight of 5,000 Da and a Mw/Mn=1.5. The weight percent contents of Folate-PEG and PCSH are about 0.30 wt % and about 0.30 wt %, respectively.

The therapeutic and biopolymer solutions are mixed to form a homogenous solution. Particles with an average diameter in the range of about 0.250 µm to about 1 µm are produced, but smaller capsules may be made by adjusting the process variables. Specifically, the flowrates used are in the range of about 0.050 to about 0.300 ml/h. The external voltage is about 7.5 kV.

Particles with a Paclitaxel loading is the range of about 0.01 to about 25% by weight of the added polymer may be made by adjusting the concentration of the core fluid solution.

Specific Example 21

Capsules with Paclitaxel with Folic Acid Functional Groups

The core fluid solution is prepared by mixing Paclitaxel in DMSO and about 10 wt % of γ-cyclodextrine in about 10 mM Bis-Tris propane aqueous solution containing about 1 wt % of isopropanol and about 2 mM of $CaCl_2$. The final concentration of Paclitaxel in the core fluid solution is about 20 µg/mL.

The shell fluid solution is prepared by mixing two functionalized biopolymers in chloroform: (a) Folate functionalized poly(ethylene glycol), or Folate-PEG, with a molar weight of 5,000 Da; and (b) Poly(caprolactone)-SH, or PCSH, with a molecular weight of 5000 Da and a Mw/Mn=1.5. The weight percent contents of Folate-PEG and PCSH are about 0.30 wt % each.

Capsules with an average diameter in the range of about 0.250 µm to about 1 µm are generated, but smaller capsules may be made by adjusting the process variables. Specifically, the core and shell fluid flow rates are about 0.050 and about 0.300 ml/h, respectively, and the external voltage is about 7.5 kV.

Capsules with a paclitaxel loading in the range of about 0.01 to about 0.2% by weight of the added polymer are made by adjusting the concentration of the core fluid solution.

Specific Example 22

Particles with Paclitaxel

The therapeutic solution is prepared by mixing Paclitaxel in dichloromethane. The concentration of Paclitaxel in the therapeutic solution is about 1,000 µg/mL.

A biopolymer solution is prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH are about 0.3 wt % and about 0.3 wt %, respectively.

The therapeutic and biopolymer solutions are mixed to form a homogenous solution. Particles with an average diameter in the range of about 0.250 µm to about 1 µm are produced, but smaller capsules may be made by adjusting the process variables. Specifically, the flowrate is in the range of about 0.050 to about 0.300 ml/h, and the external voltage is about 7.5 kV.

Particles with a Paclitaxel loading in the range of about 0.01 to about 25% by weight of the added polymer may be made by adjusting the concentration of the core fluid solution.

Specific Example 23

Encapsulation of Paclitaxel

The core fluid solution is prepared by mixing Paclitaxel in DMSO and about 10 wt % of γ-cyclodextrine in about 10 mM Bis-Tris propane aqueous solution containing about 1 wt % of isopropanol and 2 mM of $CaCl_2$. The final concentration of Paclitaxel in the core fluid solution is about 20 µg/mL.

The shell fluid solution is prepared by mixing two functionalized biopolymers in chloroform (a)COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH are about 0.3 wt % each.

Capsules with an average diameter in the range of about 0.250 µm to about 1 µm are produced, but smaller capsules may be made by adjusting the process variables. Specifically, the core and shell fluid flow rates are about 0.050 and about 0.300 ml/h, respectively, and the external voltage is about 7 kV.

Capsules with a Paclitaxel loading in the range of about 0.1 to about 0.2% by weight of the added polymer may be made by adjusting the concentration of the core fluid solution.

Specific Example 24

Encapsulation of Gold Nanoparticles

The core fluid solution is prepared by mixing an aqueous solution of gold nanoparticles, or NP-Au and a 10 mM Bis-Tris propane aqueous solution containing about 1 wt % of isopropanol and about 2 mM of $CaCl_2$. The final concentration of NP-Au in the core fluid solution is in the range of about 1,000 to about 500 µg/mL.

The shell fluid solution is prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH are about 0.30 wt % and about 0.30 wt %, respectively.

Capsules with an average diameter in the range of about 0.250 µm to about 1 µm are produced, but smaller capsules may be made by adjusting the process variables. Specifically, the core and shell fluid flow rates are about 0.050 and about 0.150 ml/h, respectively, and the external voltage is about 8 kV.

Capsules with a gold nanoparticle loading in the range of about 0.01 to about 11% by weight of the added polymer may be made by adjusting the concentration of the core fluid solution.

Specific Example 25

Encapsulation of Silver Nanoparticles

The core fluid solution is prepared by mixing an aqueous solution of silver nanoparticles, or NP-Ag and a 10 mM Bis-Tris propane aqueous solution containing about 1 wt % of isopropanol and about 2 mM of $CaCl_2$. The final concentration of NP-Ag in the core fluid solution is in the range of about 1,000 to about 500 μg/mL.

The shell fluid solution is prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH are about 0.30 wt % and about 0.30 wt %, respectively.

Capsules with an average diameter in the range of about 0.250 μm to about 1 μm are produced, but smaller capsules may be made by adjusting the process variables. Specifically, the core and shell fluid flow rates are about 0.50 and about 0.150 ml/h, respectively, and the external voltage is about 8 kV.

Capsules with a silver nanoparticle loading in the range of about 0.01 to about 11% by weight of the added polymer may be made by adjusting the concentration of the core fluid solution.

Specific Example 26

Encapsulation of Palladium Nanoparticles

The core fluid solution is prepared by mixing an aqueous solution of palladium nanoparticles, or Np—Pd and about 10 mM Bis-Tris propane aqueous solution containing about 1 wt % of isopropanol and about 2 mM of $CaCl_2$. The final concentration of NP-Pd in the core fluid solution is in the range of about 1,000 to about 500 μg/mL.

The shell fluid solution is prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH are about 0.30 wt % and about 0.30 wt %, respectively.

Capsules with an average diameter in the range of about 0.250 μm to about 1 μm are produced, but smaller capsules may be made by adjusting the process variables. Specifically, the core and shell fluid flow rates are about 0.050 and about 0.150 ml/h, respectively, and the external voltage is about 8 kV.

Capsules with a palladium nanoparticles loading in the range of about 0.01 to about 11% by weight of the added polymer may be made by adjusting the concentration of the core fluid solution.

Specific Example 27

Particles with Paclitaxel and Estradiol Functional Groups

The therapeutic solution is prepared by mixing paclitaxel in dichloromethane. The concentration of Paclitaxel in the therapeutic solution is about 1,000 μg/mL.

A biopolymer solution is prepared by mixing two functionalized biopolymers in chloroform: (a) Estradiol functionalized poly(ethylene glycol), or EST-PEG, with a molecular weight of 5,000 Da; and (b) Poly(caprolactone)-SH, or PCSH, with a molecular weight of 5,000 Da and a Mw/Mn=1.5. The weight percent contents of EST-PEG and PCSH are about 0.30 wt % each.

The therapeutic and biopolymer solutions are mixed to form a homogenous solution. Particles with an average diameter in the range of about 0.250 μto about 1 μm are produced, but smaller capsules may be made by adjusting the process variables. Specifically, the flowrate is in the range of about 0.050 to about 0.300 ml/h range, and the external voltage is about 7.5 kV.

Particles with a paclitaxel loading in the range of about 0.01 to about 25% by weight of the added polymer may be made by adjusting the concentration of the core fluid solution.

Specific Example 28

Capsules with Paclitaxel and Estradiol Functional Groups

The core fluid solution is prepared by mixing Paclitaxel in DMSO and about 10 wt % of γ-cyclodextrine in about 10 mM Bis-Tris propane aqueous solution containing about 1 wt % of isopropanol and 2 mM of $CaCl_2$. The final concentration of Paclitaxel in the core fluid solution is about 20 μg/mL.

The shell fluid solution is prepared by mixing two functionalized biopolymers in chloroform: (a) Estradiol functionalized poly(ethylene glycol), or EST-PEG, with a molar weight of 5,000 Da; and (b) Poly(caprolactone)-SH, or PCSH, with a molecular weight of 5,000 Da and a Mw/Mn=1.5. The weight percent contents of EST-PEG and PCSH are about 0.30 wt % each.

Capsules with an average diameter in the range of about 0.250 μm to about 1 μm are produced, but smaller capsules may be made by adjusting the process variables. Specifically, the core and shell fluid flow rates are about 0.050 and about 0.150 ml/h, respectively, and the external voltage is about 8 kV.

Specific Example 29

Particles with Paclitaxel and Epidermal Growth Factor Groups

The therapeutic solution is prepared by dissolving Paclitaxel in dichloromethane. The concentration of Paclitaxel in the therapeutic solution is about 1,000 μg/mL.

A biopolymer solution is prepared by mixing three functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; (b) Poly(caprolactone)-SH, or PCSH, with a molecular weight of 5,000 Da and a Mw/Mn=1.5; and (c) Epidermal growth factor-functionalized poly(ethylene glycol), or EGF-PEG, with a molecular weight of 5,000 Da. The weight percent contents of PEG-b-PLA, PCSH and EGF-PEG are about 0.30 wt %, about 0.30 wt % and about 0.10 wt %, respectively.

The therapeutic and biopolymer solutions are mixed to form a homogenous solution. Particles with an average diameter in the range of about 0.250 μm to about 1 μm are produced, but smaller capsules may be made by adjusting the process variables. Specifically, the flowrates are in the range of about 0.050 to about 0.300 ml/h. The external voltage is about 7.5 kV.

Particles with a paclitaxel loading in the range of about 0.01 to about 25% by weight of the added polymer may be made by adjusting the concentration of the core fluid solution.

Specific Example 30

Capsules with Paclitaxel and Epidermal Growth Factor Groups

The core fluid solution is prepared by mixing paclitaxel in DMSO and about 10 wt % of γ-cyclodextrine in a about 10 mM Bis-Tris propane aqueous solution containing about 1 wt % of isopropanol and 2 mM of $CaCl_2$. The final concentration of Paclitaxel in the core fluid solution is about 20 μg/mL.

The shell fluid solution is prepared by mixing three functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; (b) Poly(caprolactone)-SH, or PCSH, with a molecular weight of 5,000 Da and a Mw/Mn=1.5; and (c) Epidermal growth factor-functionalized poly(ethylene glycol), or EGF-PEG, with a molecular weight of 5,000 Da. The weight percent contents of PEG-b-PLA, PCSH and EGF-PEG are about 0.30 wt %, about 0.30 wt % and about 0.10 wt %, respectively.

Capsules with an average diameter in the range of about 0.250 μm to about 1 μm are produced, but smaller capsules may be made by adjusting the process variables. Specifically, the core and shell fluid flow rates are about 0.050 and about 0.300 ml/h, respectively, and the external voltage is about 7.5 kV.

Capsules with a paclitaxel loading in the range of about 0.01 to about 0.2% by weight of the added polymer are made by adjusting the concentration of the core fluid solution.

Specific Example 31

Encapsulation of pCMV-Luc Plasmid

The core fluid solution is prepared by mixing a buffer solution containing pCMV-Luc plasmid containing the cytomegalovirus (CMV) promoter of pcDNA3 inserted upstream to the firefly luciferase of the pGL2-basic vector plasmid with a 10 mM Bis-Tris propane aqueous solution containing about 1 wt % of isopropanol and about 2 mM of $CaCl_2$. The final concentration of pCMV-Luc in the core fluid solution is in the range of about 1 to about 1000 μg/mL.

The shell fluid solution is prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The weight percent contents of PEG-b-PLA and PCSH are about 0.30 wt % and about 0.30 wt %, respectively.

Capsules with an average diameter in the range of about 0.250 μm to about 1 μm are produced, but smaller capsules may be made by adjusting the process variables. Specifically, the core and shell fluid flow rates are about 0.050 and about 0.150 ml/h, respectively, and the external voltage is about 8 kV.

Capsules with a pCMV-Luc loading is in the range of about 0.01 to about 11% by weight of the added polymer may be made by adjusting the concentration of the core fluid solution.

Specific Example 32

Encapsulation of 425 TNF-α DNA and Bovine Serum Albumin Rhodamine Conjugate The core fluid solution was prepared by mixing 425 TNF-α DNA, and bovine serum albumin rhodamine conjugate, or BSA-rhodamine, in about 10 mM Bis-Tris propane aqueous solution containing about 1 wt % of isopropanol and about 2 mM of $CaCl_2$. The final concentration of 425 TNF-a/DNA and BSA-rhodamine in the core fluid solution were about 12.2 μg/mL, and about 200 μg/mL, respectively.

The shell fluid solution was prepared by mixing an EGF grafted to a fluorescein-labeled poly(ethylene glycol)-NHS biopolymer, or F-PEG-EGF, with a molecular weight of 3,400 Da. The amount of F-PEG-EGF in the shell fluid solution was about 0.317 wt %.

Capsules with an average diameter of about 0.41 μm were produced, but smaller capsules may be made by adjusting the process variables. Specifically, the core and shell fluid flow rates used were about 0.05 and about 0.30 ml/h, respectively, and the applied voltage was about 6.5 kV.

Capsules with a 425 TNF-α DNA loading in the range of about 0.01 to about 30% by weight of the added polymer may be made by adjusting the concentration of the core fluid solution.

Specific Example 33

Encapsulation of Temozolomide

The core fluid solution was prepared by mixing temozolomide or TMZ in about 0.1 M acetate buffer solution. The final concentration of TMZ in the core fluid solution is about 10 μM.

The shell fluid solution was prepared by mixing two functionalized biopolymers in chloroform:(a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The contents of PEG-b-PLA and PCSH in the shell fluid solution were about 0.080 wt %, about 0.086 wt %, respectively.

Capsules with an average diameter of about 1.3 μm were produced, but smaller capsules may be made by adjusting the process variables. Specifically, the core and shell fluid flow rates were about 0.05 and about 0.30 ml/h, respectively, and the applied voltage was about 8.0 kV.

Capsules with a temozolomide loading in the range of about 0.01 to about 2.4% by weight of the added polymer may be made by adjusting the concentration of the core fluid solution.

Specific Example 34

Encapsulation of TNF-α Protein and Bovine Serum Albumin Fluorescein Conjugate The core fluid solution was prepared by mixing TNF-α protein, and bovine serum albumin fluorescein conjugate, or BSA-fluor 594, in about 10 mM Bis-Tris propane aqueous solution containing about 1 wt % of isopropanol and about 2 mM of $CaCl_2$. The final concentrations of TNF-α protein and BSA-fluor in the core fluid solution were about 345 μg/mL and about 200 μg/mL, respectively.

The shell fluid solution was prepared by mixing two functionalized biopolymers in chloroform: (a) COOH-poly(ethylene glycol)-b-polylactide, or PEG-b-PLA, with a molecular weight of 2000-b-1940 Da using same nomenclature, respectively, and a Mw/Mn=1.2; and (b) Poly(caprolactone)-SH, or PCSH, with a molecular weight of 5,000 Da and a Mw/Mn=1.5. The shell fluid solution is doped with a solution of magnetite particles with an average diameter of about 15 nm. The contents of PEG-b-PLA, PCSH, and magnetite particles in the shell fluid solution were about 0.080 wt %, about 0.086 wt %, and about 0.006 respectively.

Capsules with an average diameter of about 0.225 μm and about 0.550 μm were produced, but smaller capsules may be made by adjusting the process variables. Specifically, the core and shell fluid flow rates were about 0.050 and about 0.300 ml/h, respectively, and the applied voltage was about 7.0 kV.

Capsules with a TNF-α protein loading in the range of about 0.01 to about 23% by weight of the added polymer may be made by adjusting the concentration of the core fluid solution.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the polymer sciences, molecular biology or related fields are intended to be within the scope of the appended claims.

The disclosures of all references and publications cited above are expressly incorporated by reference in their entireties to the same extent as if each were incorporated by reference individually.

What is claimed is:

1. An electrohydrodynamic system for producing a capsule having at least one encapsulated agent, said system comprising:
    a hollow tube having an external wall and an interior configured to receive a core fluid;
    a shell liquid source surrounding only a fraction of a length of the external wall of said hollow tube such that at least a discharge end of the hollow tube is not surrounded by the shell liquid source;
    a core fluid supply tube arranged to supply the core fluid to said interior of said hollow tube;
    a shell liquid supply tube arranged to supply a shell liquid to said shell liquid source;
    a collector electrode positioned above the shell liquid source configured to collect the produced capsule;
    an extractor body positioned between the shell liquid source and the collector electrode; and
    an electric potential source to subject the core fluid and the shell liquid to an electric potential to cause the core fluid and shell liquid to form a jet including an at least two-fluid electrically charged fluid by incorporation of the extractor body.

2. The system of claim 1, wherein the core fluid comprises at least one of a therapeutic agent and an imaging agent.

3. The system of claim 1, further comprising a core fluid reservoir.

4. The system of claim 1, further comprising a shell liquid reservoir.

5. The system of claim 1, wherein said shell liquid source is a shell liquid bath.

6. The system of claim 1, wherein said shell liquid source is a porous material.

7. The system of claim 6, wherein the porous material is a sponge.

8. A system for producing a capsule having at least one encapsulated agent, said system comprising:
    a plurality of hollow tubes, each hollow tube having an external wall, the plurality of hollow tubes being located adjacent each other and forming a shape;
    an encasement surrounding only a fraction of a length of the external walls of said plurality of hollow tubes such that at least discharge ends of the hollow tubes are not surrounded by the encasement, the encasement having a shape that corresponds to the shape of the plurality;
    a core fluid supply tube arranged to supply a core fluid to an interior of said plurality of hollow tubes;
    a shell fluid supply tube arranged to supply a shell fluid;
    a collector electrode configured to collect the produced capsule;
    an extractor body located between an open end of the hollow tubes and the collector electrode; and
    an electric potential source to subject the core fluid and the shell fluid to an electric potential to cause the core and shell fluids to form a jet having an at least two-fluid electrically charged fluid by incorporation of the extractor body.

9. The system of claim 8, wherein at least one of said plurality of hollow tubes are circumferentially arranged in said encasement.

10. The system of claim 9, wherein said shell supply tube is configured and arranged to supply the shell fluid to a space between two said plurality of hollow tubes.

11. The system of claim 8, wherein said plurality of hollow tubes are linearly arranged in said encasement comprising at least two plates.

12. The system of claim 11, wherein said shell supply tube is configured and arranged to supply the shell fluid to a space between two said plurality of hollow tubes.

13. The system of claim 8, the plurality of hollow tubes and the shell fluid supply tube arranged to perform upward flow electrohydrodynamics.

14. The system of claim 8, the plurality of hollow tubes and the shell fluid supply tube arranged to perform downward flow electrohydrodynamics.

15. The system of claim 8, wherein the core fluid comprises at least one of a therapeutic agent and an imaging agent.

16. The system of claim 8, further comprising a core fluid reservoir.

17. The system of claim 8, further comprising a shell fluid reservoir.

18. The system of claim 8, wherein said encasement is configured to receive and deliver the shell fluid.

* * * * *